(12) United States Patent
Konopitzky et al.

(10) Patent No.: US 6,809,179 B1
(45) Date of Patent: Oct. 26, 2004

(54) TUMOR-ASSOCIATED ANTIGEN (R11)

(75) Inventors: Renate Konopitzky, Bad Voeslau (AT); Ulrich Koenig, Vienna (AT); Wolfgang Sommergruber, Purkersdorf (AT); Thomas Woelfel, Mainz (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 0 days.

(21) Appl. No.: 09/631,863

(22) Filed: Aug. 3, 2000

Related U.S. Application Data

(60) Provisional application No. 60/154,161, filed on Sep. 15, 1999.

(30) Foreign Application Priority Data

Aug. 4, 1999 (DE) .......................... 199 36 563

(51) Int. Cl.[7] .............................. C07K 14/00
(52) U.S. Cl. .................... 530/350; 530/828; 424/185.1; 424/277.1
(58) Field of Search ................. 530/350, 828; 424/185.1, 277.1, 184.1; 514/2

(56) References Cited

FOREIGN PATENT DOCUMENTS

| WO | WO 95/04542 | 2/1995 |
|---|---|---|
| WO | WO 96/10413 | 4/1996 |
| WO | WO 97/30721 | 8/1997 |

OTHER PUBLICATIONS

Roitt et al, 1998, Immunology, 4th ed, Mosby, London, p. 7.7–7.8.*
Holmes (Exp. Opin.Invest. Drugs, 2001, 10(3):511–519).*
Herbert et al. (The Dictionary of Immunology, Academic Press, 4th edition, 1995, p. 58).*
Greenspan et al. (Nature Biotechnology 7:936–937 (1999).*
Jansen, M et al, 1995, Pediatric Res, 37 (6): 681–686.*
Alberts et al. Molecular Biology of the Cell, 3rd edition, 1994, p. 465.*
Shantz and Pegg. Int J of Biochem and Cell Biol., 1999, vol. 31, pp. 107–122.*
McClean and Hill. Eur J of Cancer, 1993, vol. 29A, pp. 2243–2248.*
Fu et al. EMBO Journal, 1996, vol. 15, pp. 4392–4401.*
Yokota, J. et al. Oncogene, 1988, vol. 3, pp. 471–475.*
Gura. Science, 1997, 278:1041–1042.*
Jain. Sci. Am., 1994, 271:58–65.*
Curti. Crit. Rev. in Oncology/Hematology, 1993, 14:29–39.*
Hartwell et al. Science, 1997, 278:1064–1068.*
Ezzell. J. NIH Res, 1995, 7:46–49.*
Spitler. Cancer Biotherapy, 1995, 10:1–3.*
Boon. Adv Can Res, 1992, 58:177–210.*
Sherman, LA et al, 1998, Critical reviews in Immunol, 18(1–2): 47–54.*

MPSRCH search report, 2002, us–09–631–863a–2.oli.rai, p. 1.*
Banfi, S., et al., "Identification and mapping of human cDNAs homologous to Drosophila mutant genes through EST database searching," *Nat. Genet.* 13:167–174, Nature Publishing Co. (1996).
Becker, D., et al., "Flow–cytometric screening for the modulation of receptor–mediated endocytosis in human dendritic cells: implications for the development of an in vitro technique for predictive testing of contact sensitizers," *J. Immunol. Methods* 203:171–180, Elsevier Science B.V. (1997).
Blake, J., et al., "Use of Combinatorial Peptide Libraries to Construct Functional Mimics of Tumor Epitopes Recognized by MHC Class–I–Restricted Cytolytic T Lymphocytes," *J. Exp. Med.* 184:121–130, The Rockefeller University Press (1996).
Boon, T., et al., "Tumor antigens recognized by T lymphocytes," *Annu. Rev. Immunol.* 12:337–365, Annual Reviews, Inc. (1994).
Bork, P. and Koonin, E.V., "Predicting functions from protein sequences–where are the bottlenecks?" *Nat. Genet.* 18:313–318, Nature America, Inc. (Apr. 1998).
Buschle, M., et al., "Transloading of tumor antigen–derived peptides into antigen–presenting cells," *Proc. Natl. Acad. Sci. USA* 94:3256–3261, National Academy of Sciences (1997).
Chen, Y.–T., et al., "A testicular antigen aberrantly expressed in human cancers detected by autologous antibody screening," *Proc. Natl. Acad. Sci. USA* 94:1914–1918, National Academy of Sciences (1997).
Gaudin, C., et al., "A hsp70–2 Mutation Recognized by CTL on a Human Renal Cell Carcinoma," *J. Immunol.* 162:1730–1738, The American Association of Immunologists (Feb. 1999).
Hogan, K.T., et al., "The Peptide Recognized by HLA–A68.2–restricted, Squamous Cell Carcinoma of the Lung–specific Cytotoxic T Lymphocytes Is Derived from a Mutated *Elongation Factor 2* Gene," *Cancer Res.* 58:5144–5150, American Cancer Society (Nov. 1998).
Jäger, M., et al., "Simultaneous Humoral and Cellular Immune Response against Cancer–Testis Antigen NY–ESO–1: Definition of human Histocompatibility Leukocyte Antigen (HLA)–A2–binding Peptide Epitopes," *J. Exp. Med.* 187:265–270, The Rockefeller University Press (Jan. 1998).
Jessup, J.M. and Loda, M., "Prognostic Markers in Rectal Carcinoma," *Semin. Surg. Oncol.* 15:131–140, John Wiley & Sons, Inc. (Sep. 1998).

(List continued on next page.)

Primary Examiner—Susan Ungar
Assistant Examiner—Minh Tam Davis
(74) Attorney, Agent, or Firm—Sterne, Kessler, Goldstein & Fox P.L.L.C.

(57) ABSTRACT

Tumor-associated antigens, immunogenic peptides derived therefrom and DNA molecules coding therefor, and the use thereof in the immunotherapy of cancers.

3 Claims, 6 Drawing Sheets

OTHER PUBLICATIONS

Kawakami, Y., et al., "Recognition of Multiple Epitopes in the Human Melanoma Antigen gp100 by Tumor–Infiltrating T Lymphocytes Associated with In Vivo Tumor Regression," *J. Immnol.* 154:3961–3968, The American Association of Immunologists (1995).

Koonin, E.V., et al., "Yeast chromosome III: new gene functions," *EMBO J.* 13:493–503, Oxford University Press (1994).

Lethé, B., et al., "*LAGE–1,* A New Gene with Tumor Specificity," Int. J. Cancer 76:903–908, John Wiley & Sons, Inc. (Jun. 1998).

Mandruzzato, S., et al., "A CASP–8 Mutation Recognized by Cytolytic T Lymphocytes on a Human Head and Neck Carcinoma," *J. Exp. Med.* 186:785–793, The Rockefeller University Press (1997).

Mayordomo, J.I., et al., "Bone marrow–derived dendritic cells pulsed with synthetic tumour peptides elicit protective and therapeutic antitumour immunity," *Nat. Med.* 1:1297–1302, Nature Publishing Co. (1995).

Murphy. G.P., et al., "Current Evaluation of the Tissue Localization and Diagnostic Utility of Prostate Specific Membrane Antigen," *Cancer* 83:2259–2269, American Cancer Society (Dec. 1998).

Pardoll, D.M., "Cancer vaccines," *Nat. Med.* 4:525–531, Nature America, Inc. (May 1998).

Parker, K.C., et al., "Scheme for Ranking Potential HLA–A2 Binding Peptides Based on Independent Binding of Individual Peptide Side–Chains," *J. Immunol.* 152:163–175, The American Association of Immunologists (1994).

Parkhurst, M.R., et al., "Improved Induction of Melanoma–Reactive CTL with Peptides from the Melanoma Antigen gp100 Modified at HLA–A*0201–Binding Residues," *J. Immunol.* 157:2359–2548, The American Association of Immunolgists (1996).

Paterson, Y. and Ikonomidis, G., "Recombinant *Listeria monocytogenes* cancer vaccines," *Curr. Opin. Immunol.* 5:664–669, Current Biology Ltd. (1996).

Rammensee, H.–G., et al., "MHC ligand and peptide motifs: first listing," *Immunogenetics* 441:178–228, Springer–Verlag (1995).

Ravaioli, A., et al., "Prognosis and prediction of response in breast cancer: the current role of the main biological markers," *Cell Prolif.* 31:113–126, Blackwell Science Ltd. (Jun. 1998).

Restifo, N.P., "The new vaccines: building viruses that elicit antitumor immunity," *Curr. Opin. Immunol.* 8:658–663, Current Biology Ltd. (1996).

Révillion, F., et al., "ERBB2 Oncogene in Human Breast Cancer and its Clinical Significance," *Eur. J. Cancer* 34:791–808, Elsevier Science Ltd. (May 1998).

Robbins, P.F. and Kawakami, Y., "Human tumor antigens recognized by T cells," *Curr. Opin. Immunol.* 8:628–636, Current Biology Ltd. (1996).

Schmidt, W., et al., "Cell–free tumor antigen peptide–based cancer vaccines," *Proc. Natl. Acad. Sci. USA* 94:3262–3267, National Academy of Sciences (1997).

Sharp, P.M. and Lloyd, A.T., "Regional base composition variation along yeast chromosome III: evolution of chromosome primary structure," *Nucl. Acids Res.* 21:179–183, Oxford University Press (1993).

Tighe, H., et al., "Gene vaccination: plasmid DNA is more than just a blueprint," *Immunol. Today* 19:89–97, Elsevier Science Ltd. (Feb. 1998).

Tüting, T., et al., "Genetically modified bone marrow–derived dendritic cells expressing tumor–associated viral or "self" antigens induce antitumor immunity in vivo," *Eur. J. Immunol.* 27:2702–2707, Wiley–VCH Verlag GmbH (1997).

Van den Eynde, B.J. and van der Bruggen, P.. "T cell defined tumor antigens," *Curr. Opin. Immunol.* 9:684–693, Current Biology Ltd. (1997).

Van den Eynde, B. and Brichard, V.G., "New tumor antigens recognized by T cells," *Curr. Opin. Immunol.* 7:674–681, Current Biology Ltd. (1995).

Wax, S.D., et al., "Identification of a Novel Growth Factor–responsive Gene in Vascular Smooth Muscle Cells," *J. Biol. Chem.* 269:13041–13047, The American Society for Biochemistry and Molecular Biology, Inc. (1994).

Wolfel, T., et al., "A p16$^{INK4a}$–Insensitive CDK4 Mutant Targeted by Cytolytic T Lymphocytes in a Human Melanoma," *Science* 269:1281–1284, American Association for the Advancement of Science (1995).

Zitvogel, L., et al., "Therapy of Murine Tumors with Tumor Peptide–pulsed Dendritic Cells: Dependence on T Cells, B7 Costimulation, and T Helper Cell 1–associated Cytokines," *J. Exp. Med.* 183:87–97, The Rockefeller University Press (1996).

Dialog File 351, Accession No. 11456955, Derwent WPI English language abstract for WO 97/30721 (Document AN1).

* cited by examiner

SEQUENCE LISTING

<160> NUMBER OF SEQ ID NOS: 102

<210> SEQ ID NO 1
<211> LENGTH: 6582
<212> TYPE: DNA
<213> ORGANISM: Homo sapiens
<220> FEATURE:
<221> NAME/KEY: 5'UTR
<222> LOCATION: (1)..(217)
<221> NAME/KEY: CDS
<222> LOCATION: (218)..(1423)
<221> NAME/KEY: Unsure
<222> LOCATION: (1424)..(1497)
<221> NAME/KEY: CDS
<222> LOCATION: (1498)..(2571)
<221> NAME/KEY: 3'UTR
<222> LOCATION: (2572)..(6582)

<400> SEQUENCE: 1

```
acacgcgctt caacttcggt tggtgtgtgt cgaagaaacc tgactgcgcc ctgaggagaa        60
cagcggagaa ggtccaccga gcctggcgaa aggtccgctg agcgggctgt cgtccggagc       120
cactccgggc tgcggagcac ccagtggaga ccgcgcctgg ctcaggtgtg ggaccccatc       180
cttcctgtct tcgcagagga gtcctcgcgt ggtgagt atg cga aat aag cgg gtt       235
                                        Met Arg Asn Lys Arg Val
                                          1               5 ttg aaa aca aaa aaa aga agg agt gga aga ggg ggc cag gat cca ggc        283
Leu Lys Thr Lys Lys Arg Arg Ser Gly Arg Gly Gly Gln Asp Pro Gly
             10                  15                  20 ctc cat ccc cac aga agt gaa gct aca gct ggg agg tct cct ccc acc        331
Leu His Pro His Arg Ser Glu Ala Thr Ala Gly Arg Ser Pro Pro Thr
         25                  30                  35 cca acc gtc acc ctg ggt ccc gac tgc cca cct cct cct cct ccc cct        379
Pro Thr Val Thr Leu Gly Pro Asp Cys Pro Pro Pro Pro Pro Pro Pro
     40                  45                  50 ccc ccc aac aac aac aac aac aac tcc aag cac acc ggc cat aag           427
Pro Pro Asn Asn Asn Asn Asn Asn Ser Lys His Thr Gly His Lys
55                  60                  65                  70 agt gcg tgt gtc ccc aac atg acc gaa cga aga agg gac gag ctc tct        475
Ser Ala Cys Val Pro Asn Met Thr Glu Arg Arg Arg Asp Glu Leu Ser
                 75                  80                  85 gaa gag atc aac aac tta aga gag aag gtc atg aag cag tcg gag gag        523
Glu Glu Ile Asn Asn Leu Arg Glu Lys Val Met Lys Gln Ser Glu Glu
             90                  95                 100 aac aac aac ctg cag agc cag gtg cag aag ctc aca gag gag aac acc        571
Asn Asn Asn Leu Gln Ser Gln Val Gln Lys Leu Thr Glu Glu Asn Thr
        105                 110                 115 acc ctt cga gag caa gtg gaa ccc acc cct gag gat gag gat gat gac        619
Thr Leu Arg Glu Gln Val Glu Pro Thr Pro Glu Asp Glu Asp Asp Asp
    120                 125                 130 atc gag ctc cgc ggt gct gca gca gct gct gcc cca ccc cct cca ata        667
Ile Glu Leu Arg Gly Ala Ala Ala Ala Ala Pro Pro Pro Pro Ile
135                 140                 145                 150 gag gaa gag tgc cca gaa gac ctc cca gag aag ttc gat ggc aac cca        715
Glu Glu Glu Cys Pro Glu Asp Leu Pro Glu Lys Phe Asp Gly Asn Pro
                155                 160                 165 gac atg ctg gct cct ttc atg gcc cag tgc cag atc ttc atg gaa aag        763
Asp Met Leu Ala Pro Phe Met Ala Gln Cys Gln Ile Phe Met Glu Lys
            170                 175                 180 agc acc agg gat ttc tca gtt gat cgt gtc cgt gtc tgc ttc gtg aca        811
Ser Thr Arg Asp Phe Ser Val Asp Arg Val Arg Val Cys Phe Val Thr
```

-continued

```
                185                 190                 195
agc atg atg acc ggc cgt gct gcc cgt tgg gcc tca gca aag ctg gag     859
Ser Met Met Thr Gly Arg Ala Ala Arg Trp Ala Ser Ala Lys Leu Glu
        200                 205                 210 cgc tcc cac tac ctg atg cac aac tac cca gct ttc atg atg gaa atg     907
Arg Ser His Tyr Leu Met His Asn Tyr Pro Ala Phe Met Met Glu Met
215                 220                 225                 230 aag cat gtc ttt gaa gac cct cag agg cga gag gtt gcc aaa cgc aag     955
Lys His Val Phe Glu Asp Pro Gln Arg Arg Glu Val Ala Lys Arg Lys
                235                 240                 245 atc aga cgc ctg cgc caa ggc atg ggg tct gtc atc gac tac tcc aat    1003
Ile Arg Arg Leu Arg Gln Gly Met Gly Ser Val Ile Asp Tyr Ser Asn
        250                 255                 260 gct ttc cag atg att gcc cag gac ctg gat tgg aac gag cct gcg ctg    1051
Ala Phe Gln Met Ile Ala Gln Asp Leu Asp Trp Asn Glu Pro Ala Leu
        265                 270                 275 att gac cag tac cac gag ggc ctc agc gac cac att cag gag gag ctc    1099
Ile Asp Gln Tyr His Glu Gly Leu Ser Asp His Ile Gln Glu Glu Leu
        280                 285                 290 tcc cac ctc gag gtc gcc aag tcg ctg tct gct ctg att ggg cag tgc    1147
Ser His Leu Glu Val Ala Lys Ser Leu Ser Ala Leu Ile Gly Gln Cys
295                 300                 305                 310 att cac att gag aga agg ctg gcc agg gct gct gca gct cgc aag cca    1195
Ile His Ile Glu Arg Arg Leu Ala Arg Ala Ala Ala Ala Arg Lys Pro
                315                 320                 325 cgc tcg cca ccc cgg gcg ctg gtg ttg cct cac att gca agc cac cac    1243
Arg Ser Pro Pro Arg Ala Leu Val Leu Pro His Ile Ala Ser His His
        330                 335                 340 cag gta gat cca acc gag ccg gtg gga ggt gcc cgc atg cgc ctg acg    1291
Gln Val Asp Pro Thr Glu Pro Val Gly Gly Ala Arg Met Arg Leu Thr
        345                 350                 355 cag gaa gaa aaa gaa aga cgc aga aag ctg aac ctg tgc ctc tac tgt    1339
Gln Glu Glu Lys Glu Arg Arg Lys Leu Asn Leu Cys Leu Tyr Cys
360                 365                 370 gga aca gga ggt cac tac gct gac aat tgt cct gcc aag gcc tca aag    1387
Gly Thr Gly Gly His Tyr Ala Asp Asn Cys Pro Ala Lys Ala Ser Lys
375                 380                 385                 390 tct tcg ccg gcg gga aac tcc ccg gcc ccg ctg tag agggaccttc         1433
Ser Ser Pro Ala Gly Asn Ser Pro Ala Pro Leu
                395                 400 agcgaccggg ccagaaataa taaggtcccc acaagatgat gcctcatctc cacacttgca  1493 agtg atg ctc cag att cat ctt ccg ggc aga cac acc ctg ttc gtc cga  1542
     Met Leu Gln Ile His Leu Pro Gly Arg His Thr Leu Phe Val Arg
             405                 410                 415 gcc atg atc gat tct ggt gct tct ggc aac ttc att gat cac gaa tat  1590
Ala Met Ile Asp Ser Gly Ala Ser Gly Asn Phe Ile Asp His Glu Tyr
                420                 425                 430 gtt gct caa aat gga att cct cta aga atc aag gac tgg cca ata ctt  1638
Val Ala Gln Asn Gly Ile Pro Leu Arg Ile Lys Asp Trp Pro Ile Leu
        435                 440                 445 gtg gaa gca att gat ggg cgc ccc ata gca tcg ggc cca gtt gtc cac  1686
Val Glu Ala Ile Asp Gly Arg Pro Ile Ala Ser Gly Pro Val Val His
        450                 455                 460 gaa act cac gac ctg ata gtt gac ctg gga gat cac cga gag gtg ctg  1734
Glu Thr His Asp Leu Ile Val Asp Leu Gly Asp His Arg Glu Val Leu
465                 470                 475                 480 tca ttt gat gtg act cag tct cca ttc ttc cct gtc gtc cta ggg gtt  1782
Ser Phe Asp Val Thr Gln Ser Pro Phe Phe Pro Val Val Leu Gly Val
                485                 490                 495
```

```
cgc tgg ctg agc aca cat gat ccc aat atc aca tgg agc act cga tct    1830
Arg Trp Leu Ser Thr His Asp Pro Asn Ile Thr Trp Ser Thr Arg Ser
        500                 505                 510 atc gtc ttt gat tct gaa tac tgc cgc tac cac tgc cgg atg tat tct    1878
Ile Val Phe Asp Ser Glu Tyr Cys Arg Tyr His Cys Arg Met Tyr Ser
        515                 520                 525 cca ata cca cca tcg ctc cca cca cca gca cca caa ccg cca ctc tat    1926
Pro Ile Pro Pro Ser Leu Pro Pro Pro Ala Pro Gln Pro Pro Leu Tyr
        530                 535                 540 tat cca gta gat gga tac aga gtt tac caa cca gtg agg tat tac tat    1974
Tyr Pro Val Asp Gly Tyr Arg Val Tyr Gln Pro Val Arg Tyr Tyr Tyr
545                 550                 555                 560 gtc cag aat gtg tac act cca gta gat gag cac gtc tac cca gat cac    2022
Val Gln Asn Val Tyr Thr Pro Val Asp Glu His Val Tyr Pro Asp His
                565                 570                 575 cgc ctg gtt gac cct cac ata gaa atg ata cct gga gca cac agt att    2070
Arg Leu Val Asp Pro His Ile Glu Met Ile Pro Gly Ala His Ser Ile
                580                 585                 590 ccc agt gga cat gtg tat tca ctg tcc gaa cct gaa atg gca gct ctt    2118
Pro Ser Gly His Val Tyr Ser Leu Ser Glu Pro Glu Met Ala Ala Leu
            595                 600                 605 cga gat ttt gtg gca aga aat gta aaa gat ggg cta att act cca acg    2166
Arg Asp Phe Val Ala Arg Asn Val Lys Asp Gly Leu Ile Thr Pro Thr
        610                 615                 620 att gca cct aat gga gcc caa gtt ctc cag gtg aag agg ggg tgg aaa    2214
Ile Ala Pro Asn Gly Ala Gln Val Leu Gln Val Lys Arg Gly Trp Lys
625                 630                 635                 640 ctg caa gtt tct tat gat tgc cga gct cca aac aat ttt act atc cag    2262
Leu Gln Val Ser Tyr Asp Cys Arg Ala Pro Asn Asn Phe Thr Ile Gln
                645                 650                 655 aat cag tat cct cgc cta tct att cca aat tta gaa gac caa gca cac    2310
Asn Gln Tyr Pro Arg Leu Ser Ile Pro Asn Leu Glu Asp Gln Ala His
                660                 665                 670 ctg gca acg tac act gaa ttc gta cct caa ata cct gga tac caa aca    2358
Leu Ala Thr Tyr Thr Glu Phe Val Pro Gln Ile Pro Gly Tyr Gln Thr
            675                 680                 685 tac ccc aca tat gcc gcg tac ccg acc tac cca gta gga ttc gcc tgg    2406
Tyr Pro Thr Tyr Ala Ala Tyr Pro Thr Tyr Pro Val Gly Phe Ala Trp
        690                 695                 700 tac cca gtg gga cga gac gga caa gga aga tca cta tat gta cct gtg    2454
Tyr Pro Val Gly Arg Asp Gly Gln Gly Arg Ser Leu Tyr Val Pro Val
705                 710                 715                 720 atg atc act tgg aat cca cac tgg tac cgc cag cct ccg gta cca cag    2502
Met Ile Thr Trp Asn Pro His Trp Tyr Arg Gln Pro Pro Val Pro Gln
                725                 730                 735 tac ccg ccg cca cag ccg ccg cct cca cca cca ccg ccg ccg cct        2550
Tyr Pro Pro Pro Gln Pro Pro Pro Pro Pro Pro Pro Pro Pro Pro
            740                 745                 750 cca tct tac agt acc ctg taa atacctgtca tgtccttcag gatctctgcc       2601
Pro Ser Tyr Ser Thr Leu
        755 ctcaaaattt attcctgttc agcttctcaa tcagtgactg tgtgctaaat tttaggctac  2661 tgtatcttca ggccacctga ggcacatcct ctctgaaacg gctatggaag gttagggcca  2721 ctctggactg gcacacatcc taaagcacca aaagacctte aacattttct gagagcaaca  2781 gagtatttgc caataaatga tctctcattt ttccaccttg actgccaatc taactaaaat  2841 aattaataag tttactttcc agccagtcct ggaagtctgg gttttacctg ccaaaacctc  2901
```

-continued

```
catcaccatc taaattatag gctgccaaat ttgctgttta acatttacag agaagctgat    2961
acaaacgcag gaaatgctga tttctttatg gaggggggaga cgaggaggag gaggacatga    3021
cttttcttgc ggtttcggta ccctcttttt aaatcactgg aggactgagg ccttattaag    3081
gaagccaaaa ttatcggtgc agtgtggaaa ggcttccgtg atcctctcgc tgcaccctta    3141
gaaacttcac cgtcttcaaa ctccatttcc atggttctgt taattctcaa ggagcagcaa    3201
ctcgactggt tctcccagga gcaggaaaaa cccttgtgac atgaaacatc tcaggcctga    3261
aaagaaagtg ctctctcaga tggactcttg catgttaaga ctatgtcttc acatcatggt    3321
gcaaatcaca tgtacccaat gactccggct ttgacacaac accttaccat catcatgcca    3381
tgatggcttc cacaaagcat taaacctggt aaccagagat tactggtggc tccagcgttg    3441
ttagatgttc atgaaatgtg accacctctc aatcaccttt gagggctaaa gagtagcaca    3501
tcaaaaggac tccaaaatcc catacccaac tcttaagaga tttgtcctgg tacttcagaa    3561
agaattttca tgagtgttct taattggctg gaaaagcacc agctgacgtt ttggaagaat    3621
ctatccatgt gtctgcctcc atatgcatct gggcatttca tcttcagtcc cctcattaga    3681
ctgtagcatt aggatgtgtg gagagaggag aaatgattta gcacccagat tcacactcct    3741
atgcctggaa gggggacatc tttgaagaag aggaattagg gctgtggaca ctgtcttgag    3801
gatgtggact tccttagtga gctccacatt acttgatggt aaccacttca aaaggatcag    3861
aatccacgta atgaaaaagg tccctctaga ggatggagct gatgtgaagc tgccaatgga    3921
tgaaaagcct cagaaagcaa ctcaaaggac tcaaagcaac ggacaacaca agagttgtct    3981
tcagcccagt gacacctctg atgtcccctg gaagctttgt gctaacctgg gactgcctga    4041
cttcctttag cctggtccct tgctactacc ttgaactgtt ttatctaacc tctcttttc    4101
tgtttaattc tttgctactg ccattgaccc tgctgcagga tttgtgtcat tttcctgcct    4161
ggttgctgag actccatttt gctgccacac acagagatgt aagaggcagg ctttaattgc    4221
caaagcacag tttgagcagt agaaaacaac atggtgtata tctcaaattg cctgacatga    4281
agaggagtct aacggtgaag tttcactttt catcagcatc atctttcaca tgttcattat    4341
catccgctct tattcttgca tgtttaaaca cttaaaattt ttagtataat ttttagtgtg    4401
ttttgaagtg gtgactaggc tttcaaaaac ttccattgaa ttacaaagca ctatccagtt    4461
cttattgtta aactaagtaa aaatgataag taacatagtg taaaatattc ctttactgtg    4521
aacttcttac aatgctgtga atgagaggct cctcagaact ggagcatttg tataataatt    4581
catcctgttc atcttcaatt ttaacatcat atataatttc aattctatca attgggcctt    4641
taaaaatcat ataaaaggat ataaaatttg aaaagagaaa cctaattggc tatttaatcc    4701
aaaacaactt ttttttttcc ttcaatggaa tcagaaagct tgtcaatcac tcatgtgttt    4761
tagagtaatt acttttaaaa tggtgcattt gtgcttctga actattttga agagtcactt    4821
ctgtttacct caagtatcaa ttcatcctcc atacatttga attcaagttg tttttttgtca    4881
aatttacagt tgtcaattga tcttcaagct gcagggtgcc tagaaatggg ccgttgtctg    4941
tagccctggc atgtgcacac ggacatttgc caccactgca agcaaaagtc tggagaagtt    5001
caccaacgac aagaacgatt agggaaaata tgctgctgtg ggttaacaac tcagaaagtc    5061
cctgatccac atttggctgt ttactaaagc ttgtgattaa cttttttggca gtgtgtacta    5121
tgctctattg ctatatatgc tatctataaa tgtagatgtt aaggataagt aattctaaat    5181
ttattattct atagttttga agtttggtta agtttccttt cactcaattg atttattttg    5241
ttgttaatca aatttatgtt aattggatcc tttaaatttt ttttggcatt ttccaacaaa    5301
```

```
aatggcttta ttcataagaa aggaaaaaaa tcaatggaat ttgatatcta aagaagttag    5361
aaagggagca aaataaaaaa cataaaggag atagatgaat tagtaagcaa atcagtagtc    5421
gagtttttca aactggcaaa attaattaat tgacttttag cccaaattta cattgttaat    5481
taaatcaaga aggaagaaga tctaagagct cccattgata ggcaagccta gagagaacta    5541
gctaaattta tcatgctagg atattgaaac acagaaagtt tacatacatt tatgaagggt    5601
caatttagtt tggacagtga ggtatttgtc ttagtggaaa aaggagaat tagtctgatc    5661 aaatcgtgaa gtaatacagt gaacttgcag gtgcacaaaa taagagggcc acatctatat    5721
ggtgcagtct ggaattctgt ttaagtttgt aggtacctct tggacttctg aattgatcca    5781
gttgtcatcc accacagaca tctcacatca gatacagaca gttccaagat tgacaacaga    5841
gaacaacctg ctggaaagac ctgggcagaa atggagagcc ctgcgggaac catgctacat    5901
tttcatctaa agagagaatg cacatctgat gagactgaaa gttctttgtt gttttagatt    5961
gtagaatggt attgaattgg tctgtggaaa attgcattgc ttttatttct ttgtgtaatc    6021
aagtttaagt aataggggat atataatcat aagcatttta gggtgggagg gactattaag    6081
taattttaag tgggtggggt tatttagaat gttagaataa tattatgtat tagatatcgc    6141
tataagtgga catgcgtact tacttgtaac cctttacccct ataattgcta tcctaaaga    6201 tttcaaataa actcggaggg aactgcaggg agaccaactt atttagagcg aattggacat    6261
ggataaaaac cccagtggga gaaagttcaa aggtgattag attaataatt taatagagga    6321
tgagtgacct ctgataaatt actgctagaa tgaacttgtc aatgatggat ggtaaatttt    6381
catggaagtt ataaaagtga taaataaaaa cccttgcttt taccccctgtc agtagccctc    6441 ctcctaccac tgaaccccat tgcccctacc cctccttcta actttattgc tgtattctct    6501
tcactctata tttctctcta tttgctaata ttgcattgct gttacaataa aaattcaata    6561
aagatttagt ggttaagtgc t                                               6582
```

<210> SEQ ID NO 2
<211> LENGTH: 401
<212> TYPE: PRT
<213> ORGANISM: Homo sapiens

<400> SEQUENCE: 2

```
Met Arg Asn Lys Arg Val Leu Lys Thr Lys Lys Arg Arg Ser Gly Arg
1               5                   10                  15

Gly Gly Gln Asp Pro Gly Leu His Pro His Arg Ser Glu Ala Thr Ala
            20                  25                  30

Gly Arg Ser Pro Pro Thr Pro Thr Val Thr Leu Gly Pro Asp Cys Pro
        35                  40                  45

Pro Pro Pro Pro Pro Pro Pro Asn Asn Asn Asn Asn Asn Asn Asn Ser
    50                  55                  60

Lys His Thr Gly His Lys Ser Ala Cys Val Pro Asn Met Thr Glu Arg
65                  70                  75                  80

Arg Arg Asp Glu Leu Ser Glu Glu Ile Asn Asn Leu Arg Glu Lys Val
                85                  90                  95

Met Lys Gln Ser Glu Glu Asn Asn Asn Leu Gln Ser Gln Val Gln Lys
            100                 105                 110

Leu Thr Glu Glu Asn Thr Thr Leu Arg Glu Gln Val Glu Pro Thr Pro
        115                 120                 125

Glu Asp Glu Asp Asp Ile Glu Leu Arg Gly Ala Ala Ala Ala Ala
    130                 135                 140
```

```
Ala Pro Pro Pro Pro Ile Glu Glu Cys Pro Glu Asp Leu Pro Glu
145                 150                 155                 160

Lys Phe Asp Gly Asn Pro Asp Met Leu Ala Pro Phe Met Ala Gln Cys
            165                 170                 175

Gln Ile Phe Met Glu Lys Ser Thr Arg Asp Phe Ser Val Asp Arg Val
            180                 185                 190

Arg Val Cys Phe Val Thr Ser Met Met Thr Gly Arg Ala Ala Arg Trp
        195                 200                 205

Ala Ser Ala Lys Leu Glu Arg Ser His Tyr Leu Met His Asn Tyr Pro
210                 215                 220

Ala Phe Met Met Glu Met Lys His Val Phe Glu Asp Pro Gln Arg Arg
225                 230                 235                 240

Glu Val Ala Lys Arg Lys Ile Arg Arg Leu Arg Gln Gly Met Gly Ser
            245                 250                 255

Val Ile Asp Tyr Ser Asn Ala Phe Gln Met Ile Ala Gln Asp Leu Asp
            260                 265                 270

Trp Asn Glu Pro Ala Leu Ile Asp Gln Tyr His Glu Gly Leu Ser Asp
        275                 280                 285

His Ile Gln Glu Glu Leu Ser His Leu Glu Val Ala Lys Ser Leu Ser
290                 295                 300

Ala Leu Ile Gly Gln Cys Ile His Ile Glu Arg Arg Leu Ala Arg Ala
305                 310                 315                 320

Ala Ala Ala Arg Lys Pro Arg Ser Pro Pro Arg Ala Leu Val Leu Pro
            325                 330                 335

His Ile Ala Ser His His Gln Val Asp Pro Thr Glu Pro Val Gly Gly
            340                 345                 350

Ala Arg Met Arg Leu Thr Gln Glu Lys Glu Arg Arg Lys Leu
        355                 360                 365

Asn Leu Cys Leu Tyr Cys Gly Thr Gly His Tyr Ala Asp Asn Cys
370                 375                 380

Pro Ala Lys Ala Ser Lys Ser Pro Ala Gly Asn Ser Pro Ala Pro
385                 390                 395                 400

Leu

<210> SEQ ID NO 3
<211> LENGTH: 357
<212> TYPE: PRT
<213> ORGANISM: Homo sapiens

<400> SEQUENCE: 3

Met Leu Gln Ile His Leu Pro Gly Arg His Thr Leu Phe Val Arg Ala
1               5                   10                  15

Met Ile Asp Ser Gly Ala Ser Gly Asn Phe Ile Asp His Glu Tyr Val
            20                  25                  30

Ala Gln Asn Gly Ile Pro Leu Arg Ile Lys Asp Trp Pro Ile Leu Val
        35                  40                  45

Glu Ala Ile Asp Gly Arg Pro Ile Ala Ser Gly Pro Val Val His Glu
50                  55                  60

Thr His Asp Leu Ile Val Asp Leu Gly Asp His Arg Glu Val Leu Ser
65                  70                  75                  80

Phe Asp Val Thr Gln Ser Pro Phe Pro Val Val Leu Gly Val Arg
            85                  90                  95

Trp Leu Ser Thr His Asp Pro Asn Ile Thr Trp Ser Thr Arg Ser Ile
            100                 105                 110
```

```
Val Phe Asp Ser Glu Tyr Cys Arg Tyr His Cys Arg Met Tyr Ser Pro
            115                 120                 125

Ile Pro Pro Ser Leu Pro Pro Ala Pro Gln Pro Pro Leu Tyr Tyr
130                 135                 140

Pro Val Asp Gly Tyr Arg Val Tyr Gln Pro Val Arg Tyr Tyr Tyr Val
145                 150                 155                 160

Gln Asn Val Tyr Thr Pro Val Asp Glu His Val Tyr Pro Asp His Arg
            165                 170                 175

Leu Val Asp Pro His Ile Glu Met Ile Pro Gly Ala His Ser Ile Pro
            180                 185                 190

Ser Gly His Val Tyr Ser Leu Ser Glu Pro Glu Met Ala Ala Leu Arg
            195                 200                 205

Asp Phe Val Ala Arg Asn Val Lys Asp Gly Leu Ile Thr Pro Thr Ile
            210                 215                 220

Ala Pro Asn Gly Ala Gln Val Leu Gln Val Lys Arg Gly Trp Lys Leu
225                 230                 235                 240

Gln Val Ser Tyr Asp Cys Arg Ala Pro Asn Asn Phe Thr Ile Gln Asn
            245                 250                 255

Gln Tyr Pro Arg Leu Ser Ile Pro Asn Leu Glu Asp Gln Ala His Leu
            260                 265                 270

Ala Thr Tyr Thr Glu Phe Val Pro Gln Ile Pro Gly Tyr Gln Thr Tyr
            275                 280                 285

Pro Thr Tyr Ala Ala Tyr Pro Thr Tyr Pro Val Gly Phe Ala Trp Tyr
290                 295                 300

Pro Val Gly Arg Asp Gly Gln Gly Arg Ser Leu Tyr Val Pro Val Met
305                 310                 315                 320

Ile Thr Trp Asn Pro His Trp Tyr Arg Gln Pro Val Pro Gln Tyr
            325                 330                 335

Pro Pro Pro Gln Pro Pro Pro Pro Pro Pro Pro Pro Pro
            340                 345                 350

Ser Tyr Ser Thr Leu
        355

<210> SEQ ID NO 4
<211> LENGTH: 31
<212> TYPE: DNA
<213> ORGANISM: Synthetic Sequence
<220> FEATURE:
<223> OTHER INFORMATION: Description of the Synthetic Sequence: Primer

<400> SEQUENCE: 4
ctagcccacc atggcatctg cagccacgtg a                              31

<210> SEQ ID NO 5
<211> LENGTH: 30
<212> TYPE: DNA
<213> ORGANISM: Synthetic Sequence
<220> FEATURE:
<223> OTHER INFORMATION: Description of the Synthetic Sequence: Primer

<400> SEQUENCE: 5
agcttcacgt ggctgcagat gccatggtgg                                30

<210> SEQ ID NO 6
<211> LENGTH: 30
<212> TYPE: DNA
<213> ORGANISM: Synthetic Sequence
<220> FEATURE:
```

-continued

<223> OTHER INFORMATION: Description of the Synthetic Sequence: Primer

<400> SEQUENCE: 6
ctagcccacc atggcatctg cagcacgtga                               30

<210> SEQ ID NO 7
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 7
agcttcacgt ggtgcagatg ccatggtgg                                29

<210> SEQ ID NO 8
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 8
ctagcccacc atggcatctg cacacgtga                                29

<210> SEQ ID NO 9
<211> LENGTH: 28
<212> TYPE: DNA
<213> ORGANISM: Synthetic Sequence
<220> FEATURE:
<223> OTHER INFORMATION: Description of the Synthetic Sequence: Primer

<400> SEQUENCE: 9
agcttcacgt gtgcagatgc catggtgg                                 28

<210> SEQ ID NO 10
<211> LENGTH: 23
<212> TYPE: DNA
<213> ORGANISM: Synthetic Sequence
<220> FEATURE:
<223> OTHER INFORMATION: Description of the Synthetic Sequence: Primer

<400> SEQUENCE: 10
gggcggtagg cgtgtacggt ggg                                      23

<210> SEQ ID NO 11
<211> LENGTH: 26
<212> TYPE: DNA
<213> ORGANISM: Synthetic Sequence
<220> FEATURE:
<223> OTHER INFORMATION: Description of the Synthetic Sequence: Primer

<400> SEQUENCE: 11
gcaactagaa ggcacagtcg aggctg                                   26

<210> SEQ ID NO 12
<211> LENGTH: 27
<212> TYPE: DNA
<213> ORGANISM: Synthetic Sequence
<220> FEATURE:
<223> OTHER INFORMATION: Description of the Synthetic Sequence: Primer

<400> SEQUENCE: 12
gtttggacag tgaggtattt gtcttag                                  27

```
<210> SEQ ID NO 13
<211> LENGTH: 27
<212> TYPE: DNA
<213> ORGANISM: Synthetic Sequence
<220> FEATURE:
<223> OTHER INFORMATION: Description of the Synthetic Sequence: Primer

<400> SEQUENCE: 13
ctttccagca ggttgttctc tgttgtc                                           27

<210> SEQ ID NO 14
<211> LENGTH: 30
<212> TYPE: DNA
<213> ORGANISM: Synthetic Sequence
<220> FEATURE:
<223> OTHER INFORMATION: Description of the Synthetic Sequence:
      synthetic Primer

<400> SEQUENCE: 14
tgacggggtc acccacactg tgcccatcta                                        30

<210> SEQ ID NO 15
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 15
ctagaagcat tgcggtggac gatggaggg                                         29

<210> SEQ ID NO 16
<211> LENGTH: 22
<212> TYPE: DNA
<213> ORGANISM: Synthetic Sequence
<220> FEATURE:
<223> OTHER INFORMATION: Description of the Synthetic Sequence: Primer

<400> SEQUENCE: 16
aaggtgaagg tcggagtcaa cg                                                22

<210> SEQ ID NO 17
<211> LENGTH: 24
<212> TYPE: DNA
<213> ORGANISM: Synthetic Sequence
<220> FEATURE:
<223> OTHER INFORMATION: Description of the Synthetic Sequence: Primer

<400> SEQUENCE: 17
ggcagagatg atgacccttt tggc                                              24

<210> SEQ ID NO 18
<211> LENGTH: 26
<212> TYPE: DNA
<213> ORGANISM: Synthetic Sequence
<220> FEATURE:
<223> OTHER INFORMATION: Description of the Synthetic Sequence: Primer

<400> SEQUENCE: 18
tattttgctc cctttctaac ttcttt                                            26

<210> SEQ ID NO 19
<211> LENGTH: 30
<212> TYPE: DNA
<213> ORGANISM: Synthetic Sequence
<220> FEATURE:
<223> OTHER INFORMATION: Description of the Synthetic Sequence: Primer
```

```
<400> SEQUENCE: 19
tttcactttt catcagcatc atctttcaca                                    30

<210> SEQ ID NO 20
<211> LENGTH: 27
<212> TYPE: DNA
<213> ORGANISM: Synthetic Sequence
<220> FEATURE:
<223> OTHER INFORMATION: Description of the Synthetic Sequence: Primer

<400> SEQUENCE: 20
cgttagactc ctcttcatgt caggcaa                                       27

<210> SEQ ID NO 21
<211> LENGTH: 22
<212> TYPE: DNA
<213> ORGANISM: Synthetic Sequence
<220> FEATURE:
<223> OTHER INFORMATION: Description of the Synthetic Sequence: Primer

<400> SEQUENCE: 21
ggtgacacta tagaaggtac gc                                            22

<210> SEQ ID NO 22
<211> LENGTH: 28
<212> TYPE: DNA
<213> ORGANISM: Synthetic Sequence
<220> FEATURE:
<223> OTHER INFORMATION: Description of the Synthetic Sequence: Primer

<400> SEQUENCE: 22
caggcctgag atgtttcatg tcacaagg                                      28

<210> SEQ ID NO 23
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 23
gcatttcctg cgtttgtatc agcttctct                                     29

<210> SEQ ID NO 24
<211> LENGTH: 30
<212> TYPE: DNA
<213> ORGANISM: Synthetic Sequence
<220> FEATURE:
<223> OTHER INFORMATION: Description of the Synthetic Sequence: Primer

<400> SEQUENCE: 24
accagcacca caaccgccac tctattatcc                                    30

<210> SEQ ID NO 25
<211> LENGTH: 30
<212> TYPE: DNA
<213> ORGANISM: Synthetic Sequence
<220> FEATURE:
<223> OTHER INFORMATION: Description of the Synthetic Sequence: Primer

<400> SEQUENCE: 25
catatagtga tcttccttgt ccgtctcgtc                                    30

<210> SEQ ID NO 26
```

```
<211> LENGTH: 26
<212> TYPE: DNA
<213> ORGANISM: Synthetic Sequence
<220> FEATURE:
<223> OTHER INFORMATION: Description of the Synthetic Sequence: Primer

<400> SEQUENCE: 26
gcgcccatca attgcttcca caagta                                        26

<210> SEQ ID NO 27
<211> LENGTH: 21
<212> TYPE: DNA
<213> ORGANISM: Synthetic Sequence
<220> FEATURE:
<223> OTHER INFORMATION: Description of the Synthetic Sequence: Primer

<400> SEQUENCE: 27
gcagagctcg tttagtgaac c                                             21

<210> SEQ ID NO 28
<211> LENGTH: 30
<212> TYPE: DNA
<213> ORGANISM: Synthetic Sequence
<220> FEATURE:
<223> OTHER INFORMATION: Description of the Synthetic Sequence: Primer

<400> SEQUENCE: 28
ggccagaaat aataaggtcc ccacaagatg                                    30

<210> SEQ ID NO 29
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 29
agctttctgc gtctttcttt ttcttcctg                                     29

<210> SEQ ID NO 30
<211> LENGTH: 26
<212> TYPE: DNA
<213> ORGANISM: Synthetic Sequence
<220> FEATURE:
<223> OTHER INFORMATION: Description of the Synthetic Sequence: Primer

<400> SEQUENCE: 30
aggtcgccaa gtcgctgtct gctctg                                        26

<210> SEQ ID NO 31
<211> LENGTH: 37
<212> TYPE: DNA
<213> ORGANISM: Synthetic Sequence
<220> FEATURE:
<223> OTHER INFORMATION: Description of the Synthetic Sequence: Primer

<400> SEQUENCE: 31
tgggtagttg tgcatcaggt agtgggagcg ctccagc                            37

<210> SEQ ID NO 32
<211> LENGTH: 27
<212> TYPE: DNA
<213> ORGANISM: Synthetic Sequence
<220> FEATURE:
<223> OTHER INFORMATION: Description of the Synthetic Sequence: Primer

<400> SEQUENCE: 32
```

```
ctcgaagggt ggtgttctcc tctgtga                                          27
```

<210> SEQ ID NO 33
<211> LENGTH: 22
<212> TYPE: DNA
<213> ORGANISM: Synthetic Sequence
<220> FEATURE:
<223> OTHER INFORMATION: Description of the Synthetic Sequence: Primer

<400> SEQUENCE: 33

```
gagctcgtcc cttcttcgtt cg                                               22
```

<210> SEQ ID NO 34
<211> LENGTH: 40
<212> TYPE: DNA
<213> ORGANISM: Synthetic Sequence
<220> FEATURE:
<223> OTHER INFORMATION: Description of the Synthetic Sequence: Primer

<400> SEQUENCE: 34

```
cataagagtg cgtgtgtccc caacatgacc gaacgaagaa                            40
```

<210> SEQ ID NO 35
<211> LENGTH: 47
<212> TYPE: DNA
<213> ORGANISM: Synthetic Sequence
<220> FEATURE:
<223> OTHER INFORMATION: Description of the Synthetic Sequence: Primer

<400> SEQUENCE: 35

```
tcgtcccttc ttcgttcggt catgttgggg acacacgcac tcttatg                    47
```

<210> SEQ ID NO 36
<211> LENGTH: 40
<212> TYPE: DNA
<213> ORGANISM: Synthetic Sequence
<220> FEATURE:
<223> OTHER INFORMATION: Description of the Synthetic Sequence: Primer

<400> SEQUENCE: 36

```
ttcttcgttc ggtcatgttg gggacacacg cactcttatg                            40
```

<210> SEQ ID NO 37
<211> LENGTH: 28
<212> TYPE: DNA
<213> ORGANISM: Synthetic Sequence
<220> FEATURE:
<223> OTHER INFORMATION: Description of the Synthetic Sequence: Primer

<400> SEQUENCE: 37

```
cagggtgacg gttggggtgg gaggagac                                         28
```

<210> SEQ ID NO 38
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 38

```
gcttcacttc tgtggggatg gaggcctgg                                        29
```

<210> SEQ ID NO 39
<211> LENGTH: 22
<212> TYPE: DNA

<213> ORGANISM: Synthetic Sequence
<220> FEATURE:
<223> OTHER INFORMATION: Description of the Synthetic Sequence: Primer

<400> SEQUENCE: 39
atgcgaaata agcgggtttt ga                                              22

<210> SEQ ID NO 40
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 40
cgcagaggag tcctcgcgtg gtgagtatg                                       29

<210> SEQ ID NO 41
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 41
ggctcaggtg tgggacccca tccttcctg                                       29

<210> SEQ ID NO 42
<211> LENGTH: 29
<212> TYPE: DNA
<213> ORGANISM: Synthetic Sequence
<220> FEATURE:
<223> OTHER INFORMATION: Description of the Synthetic Sequence: Primer

<400> SEQUENCE: 42
gctccggacg acagcccgct cagcggacc                                       29

<210> SEQ ID NO 43
<211> LENGTH: 24
<212> TYPE: DNA
<213> ORGANISM: Synthetic Sequence
<220> FEATURE:
<223> OTHER INFORMATION: Description of the Synthetic Sequence: Primer

<400> SEQUENCE: 43
gaagaaacct gactgcgccc tgag                                            24

<210> SEQ ID NO 44
<211> LENGTH: 9
<212> TYPE: PRT
<213> ORGANISM: Homo sapiens

<400> SEQUENCE: 44

Met Leu Gln Ile His Leu Pro Gly Arg
 1               5

<210> SEQ ID NO 45
<211> LENGTH: 9
<212> TYPE: PRT
<213> ORGANISM: Homo sapiens

<400> SEQUENCE: 45

Ile His Leu Pro Gly Arg His Thr Leu
 1               5

```
<210> SEQ ID NO 46
<211> LENGTH: 9
<212> TYPE: PRT
<213> ORGANISM: Homo sapiens

<400> SEQUENCE: 46

His Leu Pro Gly Arg His Thr Leu Phe
 1               5

<210> SEQ ID NO 47
<211> LENGTH: 9
<212> TYPE: PRT
<213> ORGANISM: Homo sapiens

<400> SEQUENCE: 47

Tyr Val Ala Gln Asn Gly Ile Pro Leu
 1               5

<210> SEQ ID NO 48
<211> LENGTH: 9
<212> TYPE: PRT
<213> ORGANISM: Homo sapiens

<400> SEQUENCE: 48

Leu Arg Ile Lys Asp Trp Pro Ile Leu
 1               5

<210> SEQ ID NO 49
<211> LENGTH: 9
<212> TYPE: PRT
<213> ORGANISM: Homo sapiens

<400> SEQUENCE: 49

Ile Leu Val Glu Ala Ile Asp Gly Arg
 1               5

<210> SEQ ID NO 50
<211> LENGTH: 9
<212> TYPE: PRT
<213> ORGANISM: Homo sapiens

<400> SEQUENCE: 50

Gly Arg Pro Ile Ala Ser Gly Pro Val
 1               5

<210> SEQ ID NO 51
<211> LENGTH: 9
<212> TYPE: PRT
<213> ORGANISM: Homo sapiens

<400> SEQUENCE: 51

Glu Thr His Asp Leu Ile Val Asp Leu
 1               5

<210> SEQ ID NO 52
<211> LENGTH: 9
<212> TYPE: PRT
<213> ORGANISM: Homo sapiens

<400> SEQUENCE: 52

Asp Leu Gly Asp His Arg Glu Val Leu
 1               5

<210> SEQ ID NO 53
<211> LENGTH: 9
```

```
<212> TYPE: PRT
<213> ORGANISM: Homo sapiens

<400> SEQUENCE: 53

Gly Asp His Arg Glu Val Leu Ser Phe
 1               5

<210> SEQ ID NO 54
<211> LENGTH: 9
<212> TYPE: PRT
<213> ORGANISM: Homo sapiens

<400> SEQUENCE: 54

Gln Ser Pro Phe Phe Pro Val Val Leu
 1               5

<210> SEQ ID NO 55
<211> LENGTH: 9
<212> TYPE: PRT
<213> ORGANISM: Homo sapiens

<400> SEQUENCE: 55

Val Leu Gly Pro Arg Trp Leu Ser Ala
 1               5

<210> SEQ ID NO 56
<211> LENGTH: 9
<212> TYPE: PRT
<213> ORGANISM: Homo sapiens

<400> SEQUENCE: 56

Trp Leu Ser Ala His Asp Pro Asn Ile
 1               5

<210> SEQ ID NO 57
<211> LENGTH: 9
<212> TYPE: PRT
<213> ORGANISM: Homo sapiens

<400> SEQUENCE: 57

Arg Ser Ile Val Phe Asp Ser Glu Tyr
 1               5

<210> SEQ ID NO 58
<211> LENGTH: 9
<212> TYPE: PRT
<213> ORGANISM: Homo sapiens

<400> SEQUENCE: 58

Ile Val Phe Asp Ser Glu Tyr Cys Arg
 1               5

<210> SEQ ID NO 59
<211> LENGTH: 9
<212> TYPE: PRT
<213> ORGANISM: Homo sapiens

<400> SEQUENCE: 59

Pro Pro Pro Ala Pro Gln Pro Pro Leu
 1               5

<210> SEQ ID NO 60
<211> LENGTH: 9
<212> TYPE: PRT
<213> ORGANISM: Homo sapiens
```

<400> SEQUENCE: 60

Pro Leu Tyr Tyr Pro Val Asp Gly Tyr
1               5

<210> SEQ ID NO 61
<211> LENGTH: 9
<212> TYPE: PRT
<213> ORGANISM: Homo sapiens

<400> SEQUENCE: 61

Arg Val Tyr Gln Pro Val Arg Tyr Tyr
1               5

<210> SEQ ID NO 62
<211> LENGTH: 9
<212> TYPE: PRT
<213> ORGANISM: Homo sapiens

<400> SEQUENCE: 62

Tyr Gln Pro Val Arg Tyr Tyr Tyr Val
1               5

<210> SEQ ID NO 63
<211> LENGTH: 9
<212> TYPE: PRT
<213> ORGANISM: Homo sapiens

<400> SEQUENCE: 63

Val Arg Tyr Tyr Tyr Val Gln Asn Val
1               5

<210> SEQ ID NO 64
<211> LENGTH: 9
<212> TYPE: PRT
<213> ORGANISM: Homo sapiens

<400> SEQUENCE: 64

Tyr Val Gln Asn Val Tyr Thr Pro Val
1               5

<210> SEQ ID NO 65
<211> LENGTH: 9
<212> TYPE: PRT
<213> ORGANISM: Homo sapiens

<400> SEQUENCE: 65

Glu His Val Tyr Pro Asp His Arg Leu
1               5

<210> SEQ ID NO 66
<211> LENGTH: 9
<212> TYPE: PRT
<213> ORGANISM: Homo sapiens

<400> SEQUENCE: 66

Leu Val Asp Pro His Ile Glu Met Ile
1               5

<210> SEQ ID NO 67
<211> LENGTH: 9
<212> TYPE: PRT
<213> ORGANISM: Homo sapiens

<400> SEQUENCE: 67

Glu Met Ile Pro Gly Ala His Ser Ile
1               5

<210> SEQ ID NO 68
<211> LENGTH: 9
<212> TYPE: PRT
<213> ORGANISM: Homo sapiens

<400> SEQUENCE: 68

His Ser Ile Pro Ser Gly His Val Tyr
1               5

<210> SEQ ID NO 69
<211> LENGTH: 9
<212> TYPE: PRT
<213> ORGANISM: Homo sapiens

<400> SEQUENCE: 69

Ile Pro Ser Gly His Val Tyr Ser Leu
1               5

<210> SEQ ID NO 70
<211> LENGTH: 9
<212> TYPE: PRT
<213> ORGANISM: Homo sapiens

<400> SEQUENCE: 70

Ser Leu Ser Glu Pro Glu Met Ala Ala
1               5

<210> SEQ ID NO 71
<211> LENGTH: 9
<212> TYPE: PRT
<213> ORGANISM: Homo sapiens

<400> SEQUENCE: 71

Leu Ser Glu Pro Glu Met Ala Ala Leu
1               5

<210> SEQ ID NO 72
<211> LENGTH: 9
<212> TYPE: PRT
<213> ORGANISM: Homo sapiens

<400> SEQUENCE: 72

Pro Glu Met Ala Ala Leu Arg Asp Phe
1               5

<210> SEQ ID NO 73
<211> LENGTH: 9
<212> TYPE: PRT
<213> ORGANISM: Homo sapiens

<400> SEQUENCE: 73

Glu Met Ala Ala Leu Arg Asp Phe Val
1               5

<210> SEQ ID NO 74
<211> LENGTH: 9
<212> TYPE: PRT
<213> ORGANISM: Homo sapiens

<400> SEQUENCE: 74

Ala Leu Arg Asp Phe Val Ala Arg Asn

```
                1               5
```

<210> SEQ ID NO 75
<211> LENGTH: 9
<212> TYPE: PRT
<213> ORGANISM: Homo sapiens

<400> SEQUENCE: 75

```
Val Ala Arg Asn Val Lys Asp Gly Leu
  1               5
```

<210> SEQ ID NO 76
<211> LENGTH: 9
<212> TYPE: PRT
<213> ORGANISM: Homo sapiens

<400> SEQUENCE: 76

```
Thr Ile Ala Pro Asn Gly Ala Gln Val
  1               5
```

<210> SEQ ID NO 77
<211> LENGTH: 9
<212> TYPE: PRT
<213> ORGANISM: Homo sapiens

<400> SEQUENCE: 77

```
Ile Ala Pro Asn Gly Ala Gln Val Leu
  1               5
```

<210> SEQ ID NO 78
<211> LENGTH: 9
<212> TYPE: PRT
<213> ORGANISM: Homo sapiens

<400> SEQUENCE: 78

```
Val Leu Gln Val Lys Arg Gly Trp Lys
  1               5
```

<210> SEQ ID NO 79
<211> LENGTH: 9
<212> TYPE: PRT
<213> ORGANISM: Homo sapiens

<400> SEQUENCE: 79

```
Leu Gln Val Lys Arg Gly Trp Lys Leu
  1               5
```

<210> SEQ ID NO 80
<211> LENGTH: 9
<212> TYPE: PRT
<213> ORGANISM: Homo sapiens

<400> SEQUENCE: 80

```
Tyr Pro Arg Leu Ser Ile Pro Asn Leu
  1               5
```

<210> SEQ ID NO 81
<211> LENGTH: 9
<212> TYPE: PRT
<213> ORGANISM: Homo sapiens

<400> SEQUENCE: 81

```
Glu Asp Gln Ala His Leu Ala Thr Tyr
  1               5
```

```
<210> SEQ ID NO 82
<211> LENGTH: 9
<212> TYPE: PRT
<213> ORGANISM: Homo sapiens

<400> SEQUENCE: 82

His Leu Ala Thr Tyr Thr Glu Phe Val
 1               5

<210> SEQ ID NO 83
<211> LENGTH: 9
<212> TYPE: PRT
<213> ORGANISM: Homo sapiens

<400> SEQUENCE: 83

Gly Arg Asp Gly Gln Gly Arg Ser Leu
 1               5

<210> SEQ ID NO 84
<211> LENGTH: 9
<212> TYPE: PRT
<213> ORGANISM: Homo sapiens

<400> SEQUENCE: 84

Arg Asp Gly Gln Gly Arg Ser Leu Tyr
 1               5

<210> SEQ ID NO 85
<211> LENGTH: 9
<212> TYPE: PRT
<213> ORGANISM: Homo sapiens

<400> SEQUENCE: 85

Asp Gly Gln Gly Arg Ser Leu Tyr Val
 1               5

<210> SEQ ID NO 86
<211> LENGTH: 9
<212> TYPE: PRT
<213> ORGANISM: Homo sapiens

<400> SEQUENCE: 86

Ser Leu Tyr Val Pro Val Met Ile Thr
 1               5

<210> SEQ ID NO 87
<211> LENGTH: 9
<212> TYPE: PRT
<213> ORGANISM: Homo sapiens

<400> SEQUENCE: 87

Ile Thr Trp Asn Pro His Trp Tyr Arg
 1               5

<210> SEQ ID NO 88
<211> LENGTH: 9
<212> TYPE: PRT
<213> ORGANISM: Homo sapiens

<400> SEQUENCE: 88

Ser Pro Pro Thr Pro Thr Val Thr Leu
 1               5

<210> SEQ ID NO 89
```

```
<211> LENGTH: 9
<212> TYPE: PRT
<213> ORGANISM: Homo sapiens

<400> SEQUENCE: 89

Leu Ser Glu Glu Ile Asn Asn Leu Arg
 1               5

<210> SEQ ID NO 90
<211> LENGTH: 9
<212> TYPE: PRT
<213> ORGANISM: Homo sapiens

<400> SEQUENCE: 90

Lys Leu Thr Glu Glu Asn Thr Thr Leu
 1               5

<210> SEQ ID NO 91
<211> LENGTH: 9
<212> TYPE: PRT
<213> ORGANISM: Homo sapiens

<400> SEQUENCE: 91

Leu Thr Glu Glu Asn Thr Thr Leu Arg
 1               5

<210> SEQ ID NO 92
<211> LENGTH: 9
<212> TYPE: PRT
<213> ORGANISM: Homo sapiens

<400> SEQUENCE: 92

Ile Glu Leu Arg Gly Ala Ala Ala Ala
 1               5

<210> SEQ ID NO 93
<211> LENGTH: 9
<212> TYPE: PRT
<213> ORGANISM: Homo sapiens

<400> SEQUENCE: 93

Phe Met Ala Gln Cys Gln Ile Phe Met
 1               5

<210> SEQ ID NO 94
<211> LENGTH: 9
<212> TYPE: PRT
<213> ORGANISM: Homo sapiens

<400> SEQUENCE: 94

Ser Met Met Thr Gly Arg Ala Ala Arg
 1               5

<210> SEQ ID NO 95
<211> LENGTH: 9
<212> TYPE: PRT
<213> ORGANISM: Homo sapiens

<400> SEQUENCE: 95

Ala Ala Arg Trp Ala Ser Ala Lys Leu
 1               5

<210> SEQ ID NO 96
<211> LENGTH: 9
<212> TYPE: PRT
```

<213> ORGANISM: Homo sapiens

<400> SEQUENCE: 96

Ala Lys Leu Glu Arg Ser His Tyr Leu
1               5

<210> SEQ ID NO 97
<211> LENGTH: 9
<212> TYPE: PRT
<213> ORGANISM: Homo sapiens

<400> SEQUENCE: 97

Gln Gly Met Gly Ser Val Ile Asp Tyr
1               5

<210> SEQ ID NO 98
<211> LENGTH: 9
<212> TYPE: PRT
<213> ORGANISM: Homo sapiens

<400> SEQUENCE: 98

Asn Glu Pro Ala Leu Ile Asp Gln Tyr
1               5

<210> SEQ ID NO 99
<211> LENGTH: 9
<212> TYPE: PRT
<213> ORGANISM: Homo sapiens

<400> SEQUENCE: 99

Arg Arg Leu Ala Arg Ala Ala Ala Ala
1               5

<210> SEQ ID NO 100
<211> LENGTH: 9
<212> TYPE: PRT
<213> ORGANISM: Homo sapiens

<400> SEQUENCE: 100

Lys Pro Arg Ser Pro Pro Arg Ala Leu
1               5

<210> SEQ ID NO 101
<211> LENGTH: 9
<212> TYPE: PRT
<213> ORGANISM: Homo sapiens

<400> SEQUENCE: 101

Arg Met Arg Leu Thr Gln Glu Glu Lys
1               5

<210> SEQ ID NO 102
<211> LENGTH: 9
<212> TYPE: PRT
<213> ORGANISM: Homo sapiens

<400> SEQUENCE: 102

Pro Thr Glu Pro Val Gly Gly Ala Arg
1               5

TUMOR-ASSOCIATED ANTIGEN (R11)

RELATED APPLICATION

The benefit of prior provisional application Ser. No. 60/154,161, filed Sep. 15, 1999 is hereby claimed.

FIELD OF THE INVENTION

The invention relates to a novel tumor-associated antigen (TAA), derivatives and fragments thereof, antibodies thereto, and nucleic acids encoding the TAA and its derivatives and fragments. The invention further relates to the use of such molecules in the diagnosis and treatment or prevention of tumor diseases.

BACKGROUND

The immune system has the task of protecting the body from a number of different microorganisms and actively fighting these microorganisms. The importance of an intact immune system is apparent particularly in the case of inherited or acquired immunodeficiencies. The use of prophylactic vaccine programmes proved in many cases to be an extremely effective and successful immunological intervention in the fight against viral or bacterial infectious diseases. It has also been found that the immune system is also involved to a large extent in eliminating tumour cells. Recognition of the tumour associated antigens (TAAs) by components of the immune system plays a crucial role. In the broadest sense, any (peptidic or non-peptidic) component of a tumour cell which is recognised by an element of the immune system and leads to stimulation of an immune response can act as an immunogenic tumour antigen. Those tumour antigens which not only evoke an immunological reaction but also cause rejection of the tumour are of particular importance. The identification of specific antigens which are able to provoke an immunological reaction of this kind constitutes a major step in developing a molecularly defined tumour vaccine. Although it is not yet clear which elements of the immune system are responsible for rejection of the tumour, there is nevertheless consensus that CD8-expressing cytotoxic T-lymphocytes (CTLs) play a major part (Coulie, 1997, Mol. Med. Today 3: 261–268). Particularly in those types of tumour (such as melanoma and kidney carcinoma) which have a relatively high spontaneous remission rate, a correlation has been found between the clinical progress and the increased appearance of CD8$^+$- and CD4$^+$-T-cells (Schendel et al., 1993, J. Immunol. 151: 4209–4220; Mackensen et al., 1993, Cancer Res. 53: 3569–3573; Halliday et al., 1995, World J. Surg. 19: 352–358; Kawakami et al., 1995, J. Immunol. 154: 3961–3968; Kawakami et al., 1996, Med. 45: 100–108; Wang, 1997, Mol. Med. 3: 716–731; Celluzzi and Falo, 1998, J. Immunol. 160: 3081–3085). Specific CTL clones were obtained either from tumour-infiltrating lymphocytes (TIL) or peripheral mononuclear blood cells (PBMC) after co-cultivation with generally autologous tumour cells and cytokine stimulation in vitro. Both in animal models and in human cell culture systems cultivated in vitro, the T-cell response against tumour cells was increased by transfection of tumour cells with cytokines (van Elsas et al., 1997, J. Immunother. 20: 343–353; Gansbacher et al., 1990, J. Exp. Med. 172: 1217–1224; Tepper et al., 1989, Cell 57: 503–512; Fearon et al., 1990, Cell 60: 397–403; Dranoff et al., 1993, Proc. Natl. Acad. Sci. U.S.A 90: 3539–3543).

In the light of the correlation between remission and the involvement of CD8$^+$-T cells, the identification of tumour associated antigens (TAA) which are recognised by CD8-positive CTLs is a specific prime objective towards developing a tumour vaccine (Pardoll, 1998, Nature Medcine 4: 525–531; Robbins and Kawakami, 1996, Curr. Opin. Immunol. 5: 658–63). Whether other cell types of the immune system such as for example CD4$^+$-T-helper cells play an important part is not yet clear; a number of studies with MAGE-3/HLA-A1 peptides in melanoma patients indicated this (Marchand et al., 1995, Int. J. Cancer 63: 883–885; Boon et al., 1998, Cancer Vaccine Week—International Symposium, New York, October 1998; abstract S01). In recent years a number of TAAs which are recognised by CTLs have been identified (Boon et al., 1994, Annu. Rev. Immunol. 12: 337–365; van den Eynde and van der Bruggen, 1997, Curr. Opin. Immunol. 9: 684–693).

T-cells recognise antigens as peptide fragments which are presented on the cell surfaces of MHC molecules (major histocompatibility complex, in man "HLA"="human leukocyte antigen"). There are two types of MHC molecules: MHC-I molecules occur in most cells with a nucleus and present peptides (usually 8–10-mers) which are produced by proteolytic degradation of endogenous proteins (so-called antigen processing). Peptide: MHC-I complexes are recognised by CD8-positive CTLs. MHC-II molecules occur only on so-called "professional antigen-presenting cells" (APC) and present peptides of exogenous proteins which are absorbed and processed in the course of endocytosis by APC. Peptide: MHC-II complexes are recognised by CD4-helper-T cells. By interaction between the T-cell receptor and peptide:MHC complex, various effector mechanisms may be triggered which lead to apoptosis of the target cell in the case of CTLs. This occurs if either the MHC (e.g. in the case of transplant rejection) or the peptide (e.g. in the case of intracellular pathogens) is recognised as foreign. In any case, not all the presented peptides meet the structural and functional requirements for effective interaction with T-cells (as described by Rammensee et al., 1995, Immunogenetics 41: 178–228 and hereinafter).

In principle, a number of methods of administration are possible for using TAAs in a tumour vaccine: the antigen can either be administered as a recombinant protein with suitable adjuvants or carrier systems or it may be given as cDNA coding for the antigen in plasmid (DNA vaccine; Tighe et al., 1998, Immunol. Today 19: 89–97) or viral vectors (Restifo, 1997). Another possibility is to use recombinant bacteria (e.g. listeria, salmonella) which recombinantly express the human antigen and have an adjuvant effect as a result of their additional components (Paterson, 1996, Curr. Opin. Immunol. 5: 664–669; Pardoll, 1998, Nature Medcine 4: 525–531). In all these cases, the antigen has to be processed and presented by so-called "professional antigen presenting cells" (APC). Another possibility is to use synthetic peptides (Melief et al., 1996, Curr. Opin. Immunol. 8: 651–657) which correspond to the equivalent T-cell epitopes of the antigen and are either loaded onto the APC from outside (Buschle et al., 1997, Proc. Natl. Acad. Sci. U.S.A. 94: 3256–3261; Schmidt et al., 1997, Proc. Natl. Acad. Sci. U.S.A 94: 3262–3267) or absorbed by the APC and transferred intracellularly to the MHC I molecules. The most therapeutically efficient method of administration of a specified antigen is generally determined by clinical trials.

The antigens or epitopes thereof recognised by the tumour-specific CTLs include molecules which can come from any protein classes (e.g. transcription factors, receptors, enzymes; for a survey see Rammensee et al., 1995, Immunogenetics 41: 178–228; Robbins and Kawakami, 1996, Curr. Opin. Immunol. 8: 628–636). These proteins do not necessarily have to be located on the cell surface, as is necessary for recognition by antibodies. In order to act as a tumour specific antigen for recognition by CTLs or in order to be used for therapy, the proteins must meet certain conditions: first of all, the antigen should be expressed exclusively by tumour cells or should occur in so-called "critical" normal tissues not at all or only in smaller concentrations than in tumours. Critical normal tissues are essential tissues; an immune reaction directed against them would have severe, in some cases lethal consequences. Secondly, the antigen should be present not only in the primary tumour but also in the metastases. Furthermore, with a view to broad clinical use of the antigen, it is desirable for it to be present in high concentrations in several types of tumour. One further precondition for the suitability of a TAA as an effective ingredient of a vaccine is the presence of T-cell epitopes in the amino acid sequence of the antigen; peptides derived from the TAA should lead to an in vitro/in vivo T-cell response ("immunogenic" peptide). Another criterion for selecting a clinically broadly applicable immunogenic peptide is the frequency with which the antigen is encountered in a given population of patients.

The immunogenic tumour-associated antigens (TAAs), which have already largely been shown to have T-cell epitopes, can be divided into a number of categories, including viral proteins, mutated proteins, overexpressed proteins, fusion proteins formed by chromosomal translocation, differentiation antigens, oncofoetal antigens (Van den Eynde and Brichard, 1995, Curr. Opin. Immunol. 7: 674–681; van den Eynde and van der Bruggen, 1997, Curr. Opin. Immunol. 9: 684–693).

The methods of identifying and characterising TAAs which form the starting point for the development of a tumour vaccine are based on the one hand on the use of CTLs which have already been induced in patients (cellular immune response) or antibodies (humoral immune response), or are based on drawing up differential transcription profiles between tumours and normal tissues. In the former case, the immunological approach, patient CTLs are used for screening eukaryotic tumour-cDNA expression libraries which present the CTL-epitopes via MHC-I molecules (Boon et al., 1994, Annu. Rev. Immunol. 12: 337–365), whereas by using high affinity patient antisera prokaryotic cDNA expression libraries, the presence of TAAs can be searched directly via immunoblot analysis of the individual plaques (Sahin et al., 1995, Proc. Natl. Acad. Sci. U.S.A. 92: 11810–11813). A combination of CTL reactivity and protein-chemical processes produces the isolation of peptides isolated from MHC-I from tumour cells, which are preselected by reactivity with patient CTLs. The peptides are washed out of the MHC-I complex and identified by mass spectrometry (Falk et al., 1991, Nature 351: 290–296; Woelfel et al., 1994, Int. J. Cancer 57: 413–418; Cox et al., 1994, Science 264: 716–719). The approaches which use CTLs to characterise antigens involve substantial costs or are not always successful, owing to the need to cultivate and activate CTLs. Methods of identifying TAAs which are based on comparing the transcription profile of normal and tumour tissue are many and varied; these include differential hybridization, the establishing of subtraction cDNA banks ("representational difference analysis"; Hubank and Schatz, 1994, Nucleic Acids Res. 22: 5640–5648; Diatchenko et al., 1996, Proc. Natl. Acad. Sci. U.S.A. 93: 6025–6030) and the use of DNA chip technology or the SAGE method (Velculescu et al., 1995, Science 270: 484–487). In contrast to the above-mentioned immunological method using patient CTLs, when using molecular biological methods it is necessary to show that the potential antigen candidates discovered by this method are tumour-specific (tumour-associated) and do indeed have T-cell epitopes capable of triggering a cytotoxic T-cell response. In at least one case (NY-ESO/LAGE-1) an antigen was identified both by the use of patient sera and by RDA (Chen et al., 1997, Proc. Natl. Acad. Sci. U.S.A. 94: 1914–1918; Lethe et al., 1998, Int. J. Cancer 76: 903–908), and moreover CTL-epitopes of this antigen and a simultaneous spontaneous humoral and T-cell response were described in one patient (Jager et al., 1998, J. Exp. Med. 187: 265–270).

SUMMARY OF THE INVENTION

The present invention relates to a new tumor-associated antigen designated R11. The invention further relates to R11 fragments and derivatives, nucleic acids encoding R11 and R11 fragments and derivatives, and antibodies and antibody fragments thereto which display one or more functional activities of the R11 protein such as specifically binding the R11 protein, inducing or augmenting an immune response (e.g., induction of CTLs, induction of antibodies), or treating or preventing cancer (e.g., reducing the volume or inhibiting the growth of a tumor that expresses R11).

Figure 1A:
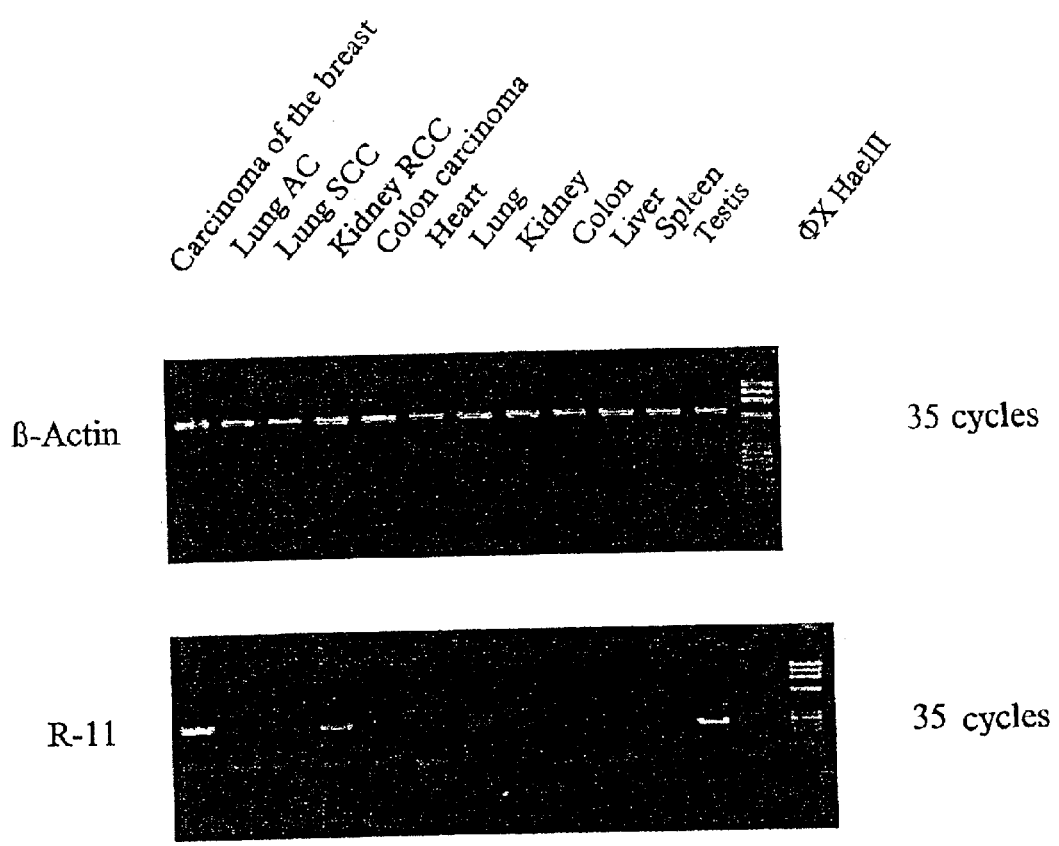
FIG. 1: Transcription of R11 in tumour tissues and normal tissues: Semi-quantitative RT-PCR

The aim of the present invention was to provide a new tumour-associated antigen (TAA).

DETAILED DESCRIPTION OF THE INVENTION

This objective was achieved by first establishing a cDNA subtraction library by RDA (representational difference analysis) between a cell line derived from a pancreas carcinoma patient and a pool of 11 different normal tissues. In order to generate the cDNA fragments of "tester" and "driver" required for the subtractive hybridisation, in a departure from the original method (Diatchenko et al., 1996, Proc. Natl. Acad. Sci. U.S.A. 93: 6025–6030) a mixture of 6 different restriction enzymes was used. The use of a mixture of different restriction enzymes which require 6 base pairs as the recognition sequence has the following advantages over the original method (Diatchenko et al., 1996, Proc. Natl. Acad. Sci. U.S.A. 93: 6025–6030): a) by selecting two restriction enzymes the recognition sequences of which are represented by combinations of 6 of the bases A/T (e.g. Ssp I: AATATT) or C/G (e.g. Nae I: GCCGGC) or A/C/G/T (e.g. EcoR V: GATATC), both GC- and AT-rich regions of a gene are cut in the same way, thus permitting homogeneous representation of the entire gene region as restriction fragments; b) in addition, this makes it possible to obtain larger cDNA fragments of the candidate gene, on a statistical average (about 800 bp), which is in turn highly advantageous in the subsequent analysis (sequencing and annotation) and cloning of the "full-size" cDNA. In the original method (Diatchenko et al., 1996, Proc. Natl. Acad. Sci. U.S.A. 93: 6025–6030) a restriction enzyme (Rsa I) recognising only 4 bases was used, which leads to an average fragment length of 256 bp and cannot specifically process CG- or AT-rich regions. In order to do justice to the hybridisation kinetics changed by the longer insert cDNA fragments, the PCR procedure was modified as described in Example 2.

In order to select the antigens which were overexpressed in the tumour, the cDNA clones obtained were first separated and a basic glycerol culture, a plasmid preparation and an insert-representing collection of the PCR fragments were established therefrom in a 96-well dish format. First, 50 randomly selected cDNA fragments of the 3450 clones of the subtractive cDNA library of the pancreatic carcinoma were sequenced in order to select the antigens which are overexpressed in the tumour and compared with sequences available in data banks. Among the genes annotated there were 12 unknown ones, for which there were EST entries (expressed sequence tags) in the data bank. One clone, R11, by its preferential presence in foetal tissue, indicated an EST profile which was suitable for possible use as a TAA. Further investigations using semi-quantitative RT-PCR and Northern Blot analysis confirmed the preferred expression in various tumour (carcinoma of the breast, kidney cells and pancreas) and immunoprivileged tissues (testis, placenta and adrenal glands) and little or no expression in normal tissues. Moreover, it can be concluded from the data obtained by Northern Blot experiments that the R11 transcript is about 7.5 kb long and that splice variants or homologous genes may possibly exist in the adrenal glands.

The human R11-cDNA was cloned from testis; the sequence obtained is shown in SEQ ID NO:1. The sequence of R11 shows no identity or homology with any known gene at either the nucleotide or protein level. The R11-cDNA obtained within the scope of the present invention contains two separate open reading frames for a protein 401 amino acids long (SEQ ID NO:2) and for a protein 357 amino acids long (SEQ ID NO:3). The R11-cDNA cloned within the scope of the present invention has a length of 6582 bp, whilst the presence of a PolyA tail at the 3'-end of the sequence is an indication of the completeness of the cDNA in this region.

On the basis of the data obtained within the scope of the present invention, it cannot be ruled out that 5' from the sequenced cDNA there is another ATG which constitutes the start ATG for the first open reading frame (R11-ORF-1); in this case, the cDNA present contains the region coding for the C-terminal section of R11-ORF-1 at the 5' end. Information as to the 5' end and a possible coding DNA sequence section located further upstream can be obtained by standard methods of molecular biology, e.g. by 5'-RACE (rapid amplification of cDNA ends). In this method, RNA, preferably mRNA, is reverse transcribed from cells or tissues in which R11 is transcribed (e.g. tissue from carcinoma of the breast, kidney cells or pancreas) and then ligated with an adapter of known sequence. A PCR with an adapter primer (binding specifically to the adapter at the 5'-end of the cDNA) and an R11-specific primer (e.g. SEQ ID NO: 26) allows corresponding R11 fragments to be amplified. These PCR products can be cloned by standard methods and characterised, particularly by DNA sequencing, as described in Example 6.

An alternative method of characterising the 5'-end is by screening cDNA libraries by hybridisation with DNA probes which are specific for R11 or analysis of cDNA expression libraries with antisera.

If the screening of cDNA libraries does not achieve the desired outcome, on account of limitations of procedure, e.g. inefficient reverse transcription caused by marked secondary structures of the RNA, genomic libraries can be searched by, for example, isolating clones, as in the screening of cDNA libraries, by hybridising with DNA probes specific for R11, said clones containing the sequence information located upstream of the 5'-end of the cDNA obtained, e.g. the promoter region of R11.

In the course of total cloning of the R11-cDNA it is possible to establish whether the open reading frame of R11-ORF-1 obtained in the region of the cDNA fragment present has a continuation in the 5' region and/or whether there are alternative reading frames.

The cDNA isolated within the scope of the present invention has the nucleotide sequence given in SEQ ID NO:1; it is to be assumed (see above) that it codes for the C-terminal portion of a tumour-associated antigen (TAA) designated R11-ORF-1 and for another protein which is represented by the second reading frame (R11-ORF-2).

The two proteins of the two reading frames expressed by the isolated cDNA have the amino acid sequence shown in SEQ ID NOs:2 and 3, respectively.

In a first aspect, the present invention relates to an isolated DNA molecule which has the nucleotide sequence shown in SEQ ID NO:1 or a polynucleotide which hybridises with this DNA molecule under stringent conditions.

By 'stringent conditions' is meant, for example: incubation overnight at 65° C.–68° C. with 6×SSC (1×SSC=150 mM NaCl, 15 mM trisodium citrate), 5×Denhardt's solution, 0.2% SDS, 50 µg/ml salmon sperm DNA, followed by washing twice for 30 min with 2×SSC, 0.1% SDS at 65° C., once for 30 min with 0.2×SSC, 0.1% SDS at 65° C. and optionally finally rinsing with 0.1×SSC, 0.1% SDS at 65° C.

In another aspect the present invention relates to an isolated DNA molecule which contains a polynucleotide of the sequence shown in SEQ ID NO: 1 as a partial sequence or which contains a polynucleotide which hybridises with a polynucleotide of this sequence under stringent conditions.

The nucleic acids or fragments thereof according to the invention code for polypeptides designated R11-ORF-1 and R11-ORF-2, whilst R11-ORF-2 has the amino acid sequence shown in SEQ ID NO:3 and R11-ORF-1 has the amino acid sequence shown in SEQ ID NO:2 or contains it; or for protein fragments or peptides derived from R11-ORF-1 or R11-ORF-2. This, therefore, includes DNA molecules which comprise deviations from the sequence shown in SEQ ID NO:1 as a result of the degeneration of the genetic code.

In another aspect the present invention relates to the tumour-associated antigens designated R11-ORF-1 and R11-ORF-2, whilst in the case of R11-ORF-1, if there is an extension of the existing open reading frame in the 5' direction, the amino acid sequence given in SEQ ID NO:2 for R11-ORF-1 is a partial sequence. The proteins with the sequences shown in SEQ ID NO: 2 and 3 are products which are translated by a transcript approximately 7.5 kb in size, or which are translated by transcripts about 3.8 kb and 2.3 kb in size which are derived from splice variants of the 7.5 kb transcript such as may be found in the adrenal tissues, or from transcripts of the genes homologous thereto.

The amino acid sequences shown in SEQ ID NO:2 and 3 may have deviations, e.g. those caused by the replacement of amino acids, insofar as the R11 derivatives ("R11", unless otherwise specified, herein denotes R11-ORF-1 and/or R11-ORF-2) have the immunogenic properties desirable for use in a tumour vaccine.

The natural amino acid sequence of R11-ORF-1 or R11-ORF-2 can optionally be modified by replacing individual amino acids in an R11 CTL-epitope in order to achieve an increase in the affinity of R11 peptides to MHC-I molecules compared with the natural R11 CTL-epitope, and thus bring about increased immunogenicity and finally greater reactivity to tumours. Modifications in the region of the R11 epitopes may be carried out on the whole R11 protein (this is processed by the APCs to form the corresponding peptides) or on larger R11 protein fragments or on R11 peptides (cf. below).

According to another aspect, the present invention relates to immunogenic polypeptide fragments and peptides derived from R11-ORF-1 or R11-ORF-2. The latter are hereinafter referred to as R11 peptides. A first group are the R11 peptides which trigger a humoral immune response (induction of antibodies). Such peptides are selected portions of R11-ORF-1 or R11-ORF-2 (at least 6 amino acids) which can be determined by so-called prediction algorithms such as for example the surface probability plot (Emini et al., 1985 J. Virol. 55: 836–839), the hydrophobicity plot (Kyte and Doolittle, 1982 J. Mol. Biol. 157: 105–132) and the antigenic index (Jameson and Wolf, 1988 Comput. Appl. Biosci. 4: 181–186).

Also included are all those peptides which are derived from the N-terminal region of R11 which is optionally obtained in the course of further cloning.

It is known that tumour-associated antigens may have tumour-specific mutations which contribute to an immunological distinction between tumour and normal tissue (Mandruzzato et al., 1997, J Exp Med 186: 785–793; Hogan et al., 1998, Cancer Res 58: 5144–5150; Gaudi et al., 1999, J Immunol 162: 1730–1738; Wolfel et al., 1995, Science 269: 1281–1284). In order to detect the presence of tumour-specific R11-ORF-1 or R11-ORF-2 mutations, the R11 cDNA is cloned from one or more different tumours, appropriately using probes of the cDNA isolated from testis according to the invention, and the sequences obtained are compared with normal tissue R11-cDNA. It is to be expected that tumour R11 peptides from a fragment of sequence which is mutated compared with normal tissue R11 will exhibit greater immunogenicity compared with normal tissue R11 peptides from the corresponding fragment. Thus, according to another aspect, the present invention relates to R11 peptides derived from regions of a tumour-expressed R11-ORF-1 or R11-ORF-2 which contain tumour-specific mutations.

For therapeutic use, R11 peptides are administered directly or in modified form (e.g. coupled to KLH (keyhole limpet hemocyanine)) and the production of antibodies is determined by common immunological assays, e.g. ELISA.

Other R11 peptides which are preferred within the scope of the present invention are those which are presented by MHC-molecules and produce a cellular immune response. There are two types of MHC-molecules, namely MHC-I molecules which are recognised by CD8-positive CTLs and MHC-II molecules which are recognised by CD4-positive T-helper cells.

In order for a peptide to trigger a cellular immune response, it must bind to an MHC-molecule, whilst the patient to be treated must have the MHC molecule in his or her repertoire. Determining the MHC-subtype of the patient thus constitutes one of the essential prerequisites for effective use of a peptide in this patient, with a view to triggering a cellular immune response.

The sequence of an R11 peptide to be used therapeutically is determined by the MHC-molecule in question in terms of the anchor amino acids and length. Defined anchor positions and length guarantee that a peptide fits the peptide binding groove of the MHC-molecule of the patient in question. The result of this is that the immune system is stimulated and a cellular immune reaction is produced which is directed against the tumour cells of the patient, if a peptide derived from a tumour antigen is used.

Immunogenic R11 peptides may be identified by known methods; one of the basic conditions is the correlation between MHC-binding and CTL-induction.

Thus, since the sequence of immunogenic peptides can be predicted on the basis of its peptide binding motif, R11 peptides which constitute CTL-epitopes can be identified and synthesised on the basis of the R11 protein sequence. Various methods are available for doing this, which are used to identify CTL-epitopes of known protein antigens; e.g. the method described by Stauss et al., 1992, Proc. Natl. Acad. Sci. U.S.A 89: 7871–7875 for identifying T-cell epitopes in human papilloma virus.

The allele-specific requirements of each MHC-I allele product with regard to a peptide which binds to the MHC-molecule and is presented thereby have been assembled as a motif (e.g. Falk et al., 1991, Nature 351: 290–296). Up until now, a large number of both MHC-peptide motifs and MHC-ligands have become known. A suitable method, within the scope of the present invention, for searching for epitopes of a known protein which fits a specific MHC-I molecule is described in a survey by Rammensee et al., 1995, Immunogenetics 41: 178–228. It comprises the following steps: first, the protein sequence is searched for fragments which correspond to the anchor motif, whilst certain variations are possible with regard to peptide length and anchor occupation. If, for example a motif prescribes a 9-mer with Ile or Leu at the end, 10-mers with a corresponding C-terminus can also be considered, as can peptides with other aliphatic groups such as Val or Met at the C-terminus. In this way a number of peptide candidates is obtained. These are searched for the presence of as many anchor groups as possible which they have in common with known ligands and/or to see whether they have groups which are "preferred" for various MHC-molecules (according to the Table by Rammensee et al., 1995, Immunogenetics 41: 178–228). In order to exclude weakly binding peptides, binding assays are preferably carried out. If the requirements for the peptide binding for specific MHC-molecules are known, the peptide candidates can also be searched for non-anchor groups which have a negative or positive effect on the binding or which indeed make it possible at all (Ruppert et al., 1993, Cell 74: 929–937). However, with this method, it should be borne in mind that the peptide binding motif is not the sole deciding factor when searching for natural ligands; other aspects, e.g. enzyme specificity during antigen processing, also contribute to the identity of the ligand, in addition to the specificity of the MHC-binding. One method which takes account of these aspects and which is suitable for identifying immunogenic R11 peptides within the scope of the present invention was used inter alia by Kawakami et al., 1995, J. Inmmunol. 154: 3961–3968 for identifying gp 100 epitopes on the basis of known HLA-A*0201 motifs.

The peptides may also be selected for their ability to bind to MHC-II molecules. The MHC-II binding motif which extends over nine amino acids has a higher degree of degeneration in the anchor positions than the MHC-I binding motif Methods have recently been developed, based on X-ray structural analysis of MHC-II molecules, which allow accurate analysis of the MHC-II binding motifs and, based on that, variations in the peptide sequence (Rammensee et al., 1995, Immunogenetics 41:178–228, and the original literature cited therein). Peptides which bind to MHC-II molecules are typically presented to the CD4-T cells by dendritic cells, macrophages or B-cells. The CD4-T-cells in turn then activate CTLs directly in sequence by the release of cytokine, for example, and increase the efficiency of antigen presentation by APC (dendritic cells, macrophages and B-cells).

Recently, databanks and prediction algorithms have become available which allow more reliable prediction of peptide epitopes which bind to a specific MHC molecule.

Within the scope of the present invention, using the algorithm described by Parker et al., 1994, J. Immunol. 152: 163 and Rammensee et al., 1995, Immunogenetics 41:178–228, candidate peptides of the C-terminal fragment of R11 have been identified for the most important HLA-types, especially for HLA-A1, -A*0201, -A3, -B7, -B14 and -B*4403, which can be expected to bind to the corresponding HLA molecules and thus constitute immunogenic CTL-epitopes; the peptides discovered are listed in Table 1. Similarly, possibly using other algorithms which take account of the different characteristics of the peptides (hydrophobicity, charge, size) or requirements made of the peptides, such as the 3D structure of the HLA-molecule, it is possible to find other potential peptide epitopes; this also applies to peptide epitopes of other HLA types.

After selecting R11-peptide candidates using the methods described, their MHC-binding is tested by peptide binding assays. First, the immunogenicity of the peptides with good binding properties is determined (stability of the peptide-MHC interaction correlates in most cases with immunogenicity; van der Burg et al., 1996, J. Immunol. 156: 3308–3314). In order to determine the immunogenicity of the selected peptide or peptide equivalent, methods may be used as described, for example, by Sette et al., 1994, J. Immunol. 153: 5586–5592 combined with quantitative MHC-binding assays. Alternatively, the immunogenicity of the selected peptide may be tested by in vitro CTL-induction using known methods (as described hereinafter for ex vivo CTL-induction). The principle of the method, carried out in several steps, for selecting peptides which are capable of triggering a cellular immune response is described in WO 97/30721, the contents of which are hereby expressly referred to. A general strategy for obtaining efficient immunogenic peptides which is suitable within the scope of the present invention has also been described by Schweighoffer, 1997, Onc. Res. 3: 164–176.

Instead of using the original peptides which fit the binding groove of MHC-I or MHC-II molecules, i.e., peptides which are derived unaltered from R11, variations may be carried out, adhering to the minimum requirements regarding anchor positions and length specified on the basis of the original peptide sequence, provided that these variations not only do not impair the effective immunogenicity of the peptide which is made up of its binding affinity to the MHC-molecule and its ability to stimulate T-cell receptors, but preferably enhance it. In this case, artificial peptides or peptide equivalents are thus used which are designed to correspond to the requirements regarding binding ability to an MHC-molecule.

Peptides modified in this way are referred to as "heteroclitic peptides". They may be obtained by the following methods:

First of all, the epitopes of MHC-I or MHC-II ligands or variations thereof are undertaken, e.g. using the principle described by Rammensee et al., 1995, Immunogenetics 41:178–228. The length of the peptide preferably corresponds to a minimum sequence of 8 to 10 amino acids with the necessary anchor amino acids, if the peptide is being matched to MHC-I molecules.

If desired, the peptide may also be extended at the C- and/or N-terminus provided that this extension does not affect the ability to bind to the MHC-molecule and the extended peptide can be cellularly processed down to the minimum sequence.

The modified peptides are then investigated for their recognition by TILs (tumour infiltrating lymphocytes), for CTL-induction and for increased MHC-binding and immunogenicity, as described by Parkhurst et al., 1996, J. Immunol 157: 2539–2548 and Becker et al., 1997, J. Immunol. Methods 203: 171–180.

Another method of finding peptides with greater immunogenicity than that of the natural R11 peptides, which is suitable for the purposes of the present invention, consists in screening peptide libraries with CTLs which recognise the R11 peptides naturally occurring on tumours, as described by Blake et al., 1996, J. Exp. Med. 184: 121–130; in connection with this it is proposed to use combinatorial peptide libraries in order to design molecules which imitate tumour epitopes recognised by MHC-I-restricted CTLs.

The R11 polypeptides according to the present invention or immunogenic fragments or peptides derived therefrom may be produced recombinantly or by peptide synthesis, as described in WO 96/10413, the disclosure of which is hereby referred to. For recombinant production, the corresponding DNA molecule is inserted by standard methods in an expression vector, transfected into a suitable host cell, the host is cultivated under suitable expression conditions and the protein is purified. Conventional methods may be used for the chemical synthesis of R11 peptides, e.g. automatic peptide synthesisers which are commercially available.

Alternatively to natural R11 peptides or heteroclitic peptides, it is also possible to use substances which imitate such peptides, e.g. "peptidomimetics" or "retro-inverse peptides". In order to test these molecules with regard to their therapeutic use in a tumour vaccine the same methods are used as described above for the natural R11 peptides or R11 peptide equivalents.

The two TAAs designated R11-ORF-1 and R11-ORF-2 according to the present invention and the protein fragments, peptides or peptide equivalents or peptidomimetics derived therefrom may be used in cancer therapy, e.g. in order to induce an immune response to tumour cells which express the corresponding antigen determinants. They are preferably used for the treatment of R11-ORF-1- and/or R11-ORF-2-positive tumours, particularly in carcinoma of the breast, kidney cells and pancreas.

The immune response in the form of induction of CTLs can be achieved in vivo or ex vivo.

In order to induce CTLs in vivo, a pharmaceutical composition containing as active component the TAAs R11-ORF-1 and/or R11-ORF-2 or fragments or a peptide or peptides derived therefrom, is administered to a patient suffering from a humoral disease associated with the TAA, whilst the quantity of TAA (peptide) must be sufficient to obtain an effective CTL response to the antigen-bearing tumour.

Thus, according to another aspect, the invention relates to a pharmaceutical composition for parenteral, topical, oral or local administration. Preferably, the composition is used parenterally, e.g. for subcutaneous, intradermal or intramuscular application, containing as active component the TAAs R11-ORF-1 and/or R11-ORF-2 or fragments or peptide(s) derived therefrom. The R11-TAAs/peptides are dissolved or suspended in a pharmaceutically acceptable, preferably aqueous, carrier. The composition may also contain conventional adjuvants such as buffers etc. The R11-TAAs/peptides may be used on their own or in conjunction with adjuvants, e.g. incomplete Freund's adjuvant, saponines, aluminium salts or, in a preferred embodiment, polycations such as polyarginine or polylysine. The peptides may also be bound to components which aid CTL induction or CTL activation, e.g. T-helper peptides, lipids or liposomes, or they are administered together with these substances and/or together with immunostimulant substances, e.g. cytokines (IL-2, IFN-γ). Methods and formulations which are suitable for the preparation and administration of the pharmaceutical composition according to the invention are described in WO 95/04542 and WO 97/30721, the disclosures of which are hereby referred to.

R11 polypeptide fragments or R11 peptides may also be used to trigger a CTL response ex vivo. An ex vivo CTL response to a tumour which expresses the two possible proteins of R11 is induced by incubating the CTL-precursor cells together with APCs and R11 peptides or R11 protein. The activated CTLs are then allowed to expand, whereupon they are re-administered to the patient. Alternatively, APCs may be loaded with R11 peptides, which may lead to efficient activation of cellular immune reactions against R11 positive tumours (Mayordomo et al., 1995, Nature Medicine 1: 1297–1302; Zitvogel et al., 1996, J. Exp. Med. 183: 87–97). One suitable method of loading peptides onto cells, e.g. dendritic cells, is disclosed in WO 97/19169.

In one embodiment of the invention a combination of several different R11 peptides or R11 peptide equivalents is used. In another embodiment, R11 peptides are combined with peptides derived from other TAAs. The choice of peptides for such combinations is made in the light of detecting different MHC-types in order to cover the broadest possible patient population, and/or it is aimed at the broadest possible spectrum of indications, by combining peptides from several different tumour antigens. The number of peptides in a pharmaceutical composition can fluctuate over a wide range, but typically a clinically usable vaccine contains 1 to 15, preferably 3 to 10 different peptides.

The peptides according to the invention may also be used as diagnostic reagents. For example, the peptides may be used to test the response of a patient to the humoral or cellular immune response evoked by the immunogenic peptide. This provides a possibility of improving a treatment procedure. For example, depending on the form of administration (peptide, total protein or DNA vaccine) of the TAA, the increase of precursor T-cells in the PBLs which show reactivity against the defined peptide epitope can be investigated (Robbins and Kawakami, 1996, Curr. Opin. Immunol. 8: 628–636 and the references cited therein). Moreover, the peptides or the total protein or antibodies directed against the TAA may be used to characterise the progression of an R11-ORF-1- or R11-ORF-2-positive tumour (e.g. by immunohistochemical analyses of primary tumour and metastases). A strategy of this kind has already proved successful in many cases, e.g. detecting the oestrogen receptor as the basis for deciding on endocrine therapy in breast cancer; c-erbB-2 as the relevant marker in the prognosis and course of therapy in breast cancer (Ravaioli et al., 1998, Cell. Prolif. 31: 113–126; Revillion et al., 1998, Eur. J. Cancer 34: 791–808); PSMA (prostate specific membrane antigen) as a marker for epithelial cells of prostate carcinoma in the serum or by using a $^{111}$In-labelled monoclonal antibody against PSMA in immunoscintigraphy on prostate carcinoma (Murphy et al., 1998, Cancer 83: 2259–2269 and references included therein); CEA (carcinoembryonic antigen) as a serological marker for the prognosis and progression in patients suffering from colorectal carcinoma (Jessup and Loda, 1998, Semin. Surg. Oncol. 15: 131–140).

Of the DNA molecules according to the invention defined above, those which lead, by mutation, to an exchange of amino acids in the protein sequence shown in SEQ ID NO:2 or 3, if they code for an R11 derivative or fragments or peptides with the immunogenic properties which are desirable for their use as tumour vaccines, are also included.

The R11 DNA molecules of the present invention or the corresponding RNAs which are also a subject of the present invention are used, like the (poly)peptides coded by them, for immunotherapy of cancer diseases.

In one embodiment of the invention, DNA molecules are used which code for natural R11 polypeptides. Alternatively to the natural R11 cDNA or fragments thereof it is possible to use modified derivatives. These comprise sequences with modifications which code for a protein (fragment) or peptides with greater immunogenicity, whilst the same considerations apply to modifications at the DNA level as apply to the peptides described above. Another type of modification is the lining up of numerous sequences coding for immunologically relevant peptides like a string of beads (Toes et al., 1997, Proc. Natl. Acad. Sci. U.S.A. 94: 14660–14665). The sequences may also be modified by the addition of auxiliary elements, e.g. functions, which ensure more efficient release and processing of the immunogen (Wu et al., 1995, Proc. Natl. Acad. Sci. U.S.A. 92: 11671–11675). For example, the processing and hence the presentation and finally the imnmunogenicity of the antigen can be increased by the addition of a locating sequence in the endoplasmatic reticulum ("ER targeting sequence").

In another aspect, the present invention relates to a recombinant DNA molecule which contains the R11-DNA according to SEQ ID NO:1 or a partial sequence, particularly the sequence coding for the polypeptide R11-ORF-1 or R11-ORF-2.

The R11 DNA molecules of the present invention may be administered, preferably in recombinant form as plasmids, directly or as part of a recombinant virus or bacterium. In theory, any method of gene therapy may be used for immunotherapy of cancer based on DNA ("DNA vaccine") on R11-DNA, both in vivo and ex vivo.

Examples of in vivo administration are the direct injection of "naked" DNA, either by intramuscular route or using a gene gun, which has been shown to lead to the formation of CTLs against tumour antigens. Examples of recombinant organisms are vaccinia virus, adenovirus or listeria monocytogenes (a summary was provided by Coulie, 1997, Mol. Med. Today 3: 261–268). Moreover, synthetic carriers for nucleic acids such as cationic lipids, microspheres, micropellets or liposomes may be used for in vivo administration of nucleic acid molecules coding for R11 peptide. As with peptides, different adjuvants which enhance the immune response may also be administered, e.g. cytokines, either in the form of proteins or plasmids coding for them. The application may optionally be combined with physical methods, e.g. electroporation.

An example of ex vivo administration is the transfection of dendritic cells as described by Tuting, 1997, Eur. J. Immunol. 27: 2702–2707, or other APCs which are used as cellular cancer vaccines.

Thus, according to another aspect, the present invention relates to the use of cells which express R11, either per se or, in optionally modified form, after transfection with the corresponding coding sequence, in order to produce a cancer vaccine.

In another aspect, the invention relates to antibodies against R11-ORF-1 or R11-ORF-2 (hereinafter 'anti-R11-antibodies') or fragments thereof. Polyclonal anti-R11-antibodies are conventionally obtained by immunising animals, particularly rabbits, by injecting the antigen or fragments thereof and subsequently purifying the immunoglobulin.

Monoclonal anti-R11-antibodies may be obtained by standard procedures following the principle described by Köhler and Milstein, 1975 Nature 265: 495–497, by immunising animals, particularly mice, then immortalising antibody-producing cells from the immunised animals, e.g. by fusion with myeloma cells, and screening the supernatant of the hybridomas obtained by immunological standard assays for monoclonal anti-R11-antibodies. For therapeutic or diagnostic use in humans, these animal antibodies may optionally be chimerised in the conventional way (Neuberger et al., 1984 Nature 312: 604–608, Boulianne et al., 1984 Nature 312: 643–646) or humanised (Riechmann et al., 1988, Nature 332: 323–327, Graziano et al., 1995, J. Immunol. 155: 4996–5002).

Human monoclonal anti-R11-antibodies (or fragments thereof) may also be obtained from so-called phage display libraries (Winter et al., 1994, Annu. Rev. Immunol. 12: 433–455, Griffiths et al., 1994, EMBO J. 13: 3245–3260, Kruif et al., 1995, Proc. Natl. Acad. Sci. USA 92: 3938–3942, McGuiness et al., 1996, Nature Biotechnol. 14: 1149) and by means of transgenic animals (Brüggemann et al., 1996 Immunol. Today 17: 391–397, Jakobovits et al., 1995, Curr. Opin. Biotechnol. 6: 561–566).

The anti-R11-antibodies according to the invention may be used in immunohistochemical analyses for diagnostic purposes.

In another aspect, the invention relates to the use of R11-ORF-1- and R11-ORF-2-specific antibodies for selectively bringing any desired substances to or into a tumour which expresses R11-ORF-1 and/or R11-ORF-2. Examples of such substances are cytotoxic agents or radioactive nuclides the activity of which consists in damaging the tumour in situ. Because of the tumour-specific expression of R11-ORF-1 or R11-ORF-2, no or very few side effects can be expected. According to another aspect, substances for detecting tumours which express R11 may be used, with the aid of R11-ORF-1 and/or R11-ORF-2 antibodies. This is useful for the diagnosis and evaluation of the treatment. Therapeutic and diagnostic uses of, are described in WO 95/33771.

The TAAs designated R11-ORF-1 and R11-ORF-2 according to the present invention and the protein fragments, peptides or peptide equivalents or peptidomimetics derived therefrom may be used in cancer therapy, e.g. to induce an immune response to tumour cells which express the corresponding antigen determinants. They are preferably used for the treatment of R11-ORF-1- and/or R11-ORF-2-positive tumours, particularly in carcinoma of the breast, kidney cells and pancreas.

In another application, R11 may be used as the target molecule of targeted chemotherapy.

By chemotherapy is meant the therapeutic administration of substances which have either a cytostatic or cytotoxic-cytolytic activity by interfering with the metabolism of malignant cells, their signal transduction and their cell division processes.

In principle, these chemotherapeutic agents develop their activity in all dividing cells; tumour cells, however, show greater sensitivity to these substances than healthy cells, as it is mainly strongly proliferating cells which are affected.

The prerequisite for the use of the tumour-associated R11 as a target for the chemotherapy is—unlike the immunological therapeutic approaches mentioned above—knowledge of the function of the R11 proteins R11-ORF-1 and R11-ORF-2 or the gene coding therefor.

The first step in the so-called 'downstream' functional analysis of R11 is conveniently a bioinformatic analysis which points the way for the experimental validation of R11 as a target for the chemotherapy.

The bioinformatic concepts based on similarity and modular structure constitute an essential basis for this analysis. Established bioinformatic aids for determining similarities are BLAST (http://www.ncbi.nlm.nih.gov/BLAST, Altschul et al., 1997, Nucleic Acids Res. 25: 3389–3402) or FASTA (Pearson & Lipman, 1988, Proc. Natl. Acad. Sci. USA 85: 2444–2448), the specialised data banks such as Pfam (http://www.sanger.ac.uk/Pfam, Bateman et al., 2000, Nucleic Acids Res. 28: 263–266) and SMART (http://smart.embl-heidelberg.de, Schultz et al., 2000, Nucleic Acids Res. 28: 231–234), which take account of domain structures. To refine the analysis, applications such as: Clustal (http://www2.ebi.ac.uk/clustalw, Higgins et al., 1996, Methods Enzymol. 266: 383–402); HMMer (http://hmmer.wustl.edu, Durbin et al, 1998, Cambridge University Press; PSI-BLAST (Altschul et al., 1997, Nucleic Acids Res. 25: 3389–3402) and the PROSITE data bank (http://www.expasy.ch/prosite, Hofmann et al., 1999, Nucleic Acids Res. 27: 215–219) may be used. Statistical methods of analysis which are not based on homologies make it possible to predict other structure- and function-related properties such as the secondary structure and the occurrence of transmembrane segments and helix-turn-helix motifs. Methods of predicting the secondary structure of proteins are available; particularly worth mentioning is Jpred (http://barton.ebi.ac.uk/servers/jpred.html, Cuff et al., 1998, Bioinformatics 14: 892–893). The prediction of the secondary structure may form the basis for functional hypotheses, e.g. if the structure of the presumed homologue is known.

Subsequently, R11 is subjected to a biochemical and biological analysis.

After the sequence analysis described above has been carried out, R11-ORF-1 and R11-ORF-2 are subjected to biochemical and biological analysis. The choice of the methods used for the further analyses depends on the result of the bioinformatic analysis carried out.

One example of functional analysis is the analysis of partly theoretically derived proteins of chromosome III of the yeast genome. (In such an analysis it was possible to predict more than 70% of the gene functions by the use of the bioinformatics, some of which were confirmed experimentally (Bork et al., 1992, Nature Genetics 18: 313–318; Sharp et al., 1993, Nucleic Acids Res. 21: 179–183 and Koonin et al., 1994, EMBO J. 13: 493–503).

In all the studies to be carried out it is important to preselect those domains of the protein of unknown function which is to be analysed which have a striking structural complexity, as limited structural information (e.g. globular regions) does not contribute to any major information content. An extensive summary of examples of successful predictions of function on the basis of protein sequences has been published in Nature Genetics by Bork and Koonin (Bork and Koonin, 1998, Nature Genetics 18: 313–318).

In the functional analysis of R11-ORF-1 carried out within the scope of the present invention it was established that, according to bioinformatic analysis, it is a protein which belongs to the family of the zinc finger-containing transcription factors.

By means of suitable experiments such as, for example, mobility shift, South-Western, UV-crosslinking, etc., it is possible to demonstrate a direct and/or indirect interaction with nucleic acids, particularly in promoter regions. Suitable methods for this are known from the literature (e.g. Ausubel et al., 1994, Vol. 1 and 2 "Current Protocols in Molecular Biology", John Wiley & Sons., Inc.).

For the first 280 amino acids of the protein derived from the R11-ORF-2 region it was possible to show a clear homology with a retroviral pol polyprotein. Thus, R11-ORF-2 might be a possible retrotransposon. Once the function of R11-ORF-1 or R11-ORF-2 is established, the significance of the R11 gene and its function or the function of the proteins coded thereby for the occurrence of tumours is analysed. This may be demonstrated, for example, by proliferation assays in vitro or in animal models using tumour cells which overexpress the gene under investigation (constitutively or inducibly) and as a control express it either in deleted (inactive) form or down-regulate it by antisense (cf. e.g. Grosveld and Kollias, 1992, Transgenic Animals, Academic Press).

R11 can be used in screening assays for identifying substances which modulate, especially inhibit, the activity of R11-ORF-1 or R11-ORF-2. In one embodiment an assay of this kind might consist, for example, of introducing R11-ORF-1 or R11-ORF-2 or an active fragment thereof into cells which react to the activity of R11 with proliferation or expressing the corresponding R11-cDNA-fragment in the cell and determining the proliferation of the cells in the presence and absence of a test substance.

One example of test cells is cells with a low division rate, e.g. primary cells which have no endogenous R11. In order to establish the suitability of cells for a screening assay, they are transformed with R11-cDNA, cultured and tested with standard assays, e.g. thymidine incorporation, for their ability to proliferate. On the basis of a significant increase in their ability to proliferate after R11 expression, they may be used as test cells, e.g. in High Throughput Screening Proliferation Assays. Examples of proliferation assays in the High Throughput format, e.g. based on the MTS assay, are described in WO 98/00713.

R11 inhibitors with a proliferation-inhibiting activity can be used to treat tumours with powerful R11 expression, particularly in carcinoma of the breast, kidney cell or pancreas.

In another aspect, the invention relates to a kit comprising in one or more containers a molecule consisting of a polypeptide comprising the amino acid sequence of SEQ ID NO:2 or SEQ ID NO:3 or a protein fragment derived from R11 or a derivative thereof; and in another container, an antibody that specifically binds to a TAA designated R11 or a fragment or derivative thereof.

EXAMPLE 1

Cell Culture of the Cell Line MZ.PC2 m7#1 B7.1 #3 Derived from a Human Pancreatic Carcinoma and Isolation of the Poly A+RNA The cell line MZ.PC2 m7#1 B7.1#3 is derived from a human pancreatic carcinoma (MZ.PC2); it was obtained as follows: First, the tumour cells were passaged once through the mouse and a clone was selected for further study (MZ.PC 2m7#1). This clone was transfected under standard conditions (Ausubel et al., 1994, Vol. 1 and 2 "Current Protocols in Molecular Biology" John Wiley & Sons, Inc.) with a eukaryotic vector (pEF-BOS; promoter originates from the human EF-1 alpha gene, selection marker puromycin; Mizushima and Nagata, 1990, Nucleic Acids Res. 18: 5322), which contains the cDNA of the human B7.1 gene (Selvakumar et al., 1992, Immunogenetics 36: 175–181). A clone MZ-PC2 m7#1 B7.1#3 was selected and cultured in T150 cell culture flasks. The nutrient medium used was RPMI 1640 (Gibco plus 4 g/L glucose) containing 10% heat-inactivated foetal calf serum and 2 mM of L-glutamine. Every 3 to 4 days the cells were cleaved for propagation by trypsinisation at 1:5. After about 80% confluence had been achieved 4 ml of a trypsin solution (containing per liter: 8 g NaCl, 0.2 g KCl, 1.13 g $Na_2HPO_4$-anhydrous, 0.2 g $KH_2PO_4$, 100 ml 2.5% trypsin solution, 1 g of EDTA-Na-salt; pH 7.2–7.4) were added to each T150 cell culture flask to harvest the cells. In all, $2\times10^7$ cells were used to isolate the RNA according to the manufacturer's instructions (RNeasy Minikit, QIAgen). Starting from about 100 µg of total-RNA the manufacturer's instructions were followed in order to isolate polyA+RNA using the Oligotex Kit (QIAgen). Then starting with about 0.5 mg of polyA+RNA the cDNA synthesis was carried out according to the manufacturer's instructions (Clontech Marathon Protokoll).

EXAMPLE 2

Representational Difference Analysis (RDA) of the Pancreatic Carcinoma Cell Line MZ.PC2 m7#1 B7.1#3 Versus a Pool of 11 Normal Tissues Starting from about 0.5 µg of poly-A(+) of the pancreatic tumour cell line MZ.PC2 m7#1 B7.1#3 and a pool of 2.5 µg of poly-A(+) RNA from 11 normal tissues (Clontech)—bone marrow, heart, kidney, liver, lung, pancreas, skeletal muscle, spleen, thymus, small intestine and stomach—RDA was carried out (Diatchenko et al. 1996, Proc. Natl. Acad. Sci. U.S.A. 93: 6025–6030; Hubank and Schatz, 1994, Nucleic. Acids. Res. 22: 5640–5648) using the PCR-select™ Kit (Clontech, Palo Alto) in accordance with the manufacturer's instructions: RNA from the pancreatic tumour cell line was used as the "tester" and RNA from the normal tissue pool was used as the "driver" in accordance with the manufacturer's instructions. In contrast to the original procedure, after the synthesis of double-stranded cDNA using oligo-dT, the cDNA was cut with 6 restriction enzymes: EcoRV, NaeI, NruI, ScaI (Promega), SspI, StuI (TaKaRa) in Promega buffer A for 2 hours at 37° C. and, after increasing the NaCl concentration to 150 mM, for a further 2 hours at 37° C. The use of this mixture of 6 different restriction enzymes made it possible to generate cDNA fragments about 800 bp long, which were used for the representational difference analysis.

Figure 5:
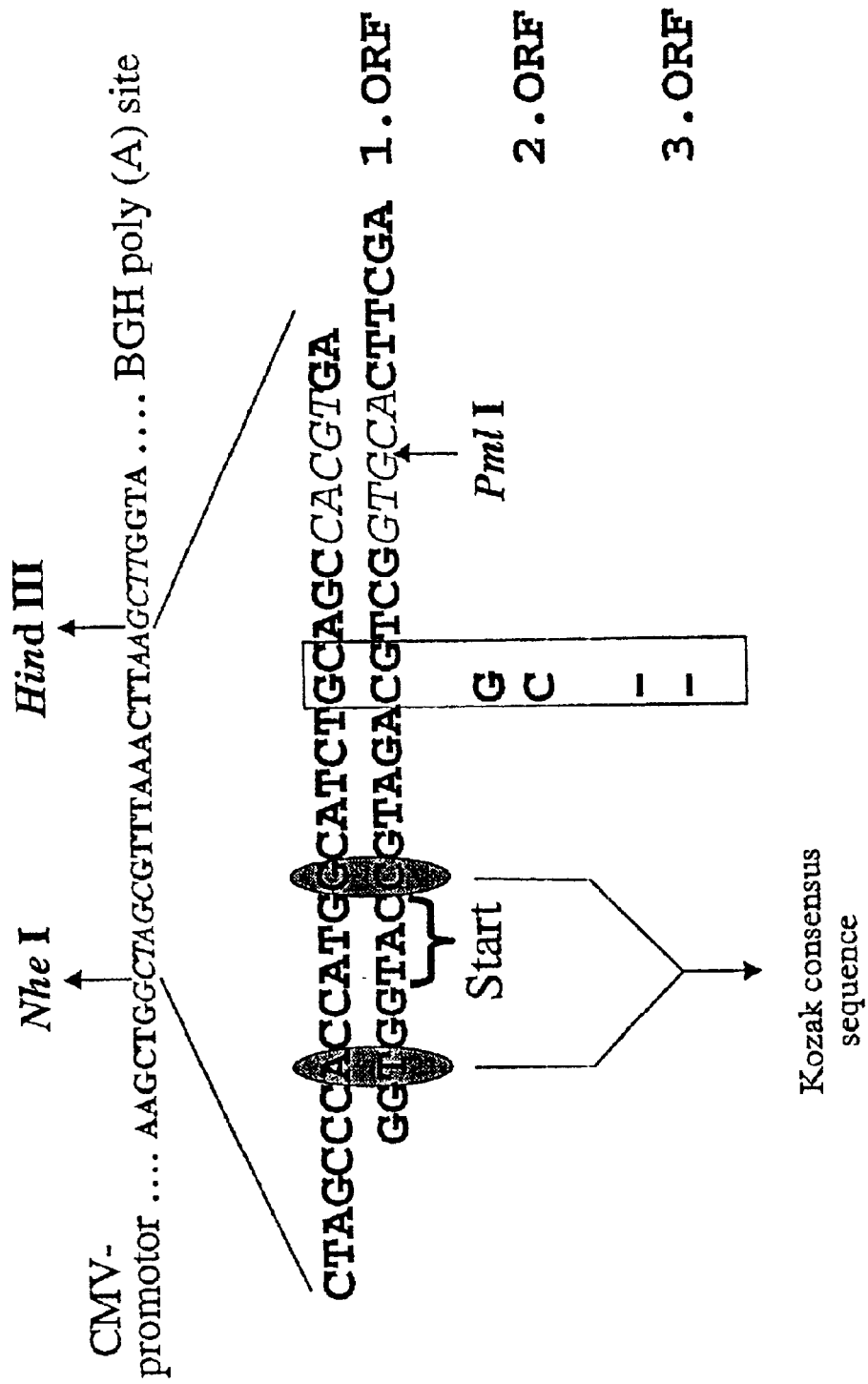
FIG. 5: Modified region of the pCR3.1(+) vector.

Equal parts of tester cDNA were ligated with either adaptor A or B and then hybridised separately with an excess of driver-cDNA at 68° C. Then the two mixtures were combined and subjected to a second hybridisation with fresh denatured driver cDNA. The concentrated tester-specific cDNAs were then amplified exponentially by PCR with primers from the kit specific for the adaptor A or B with a 2 minute elongation time at 72° C., over 27 cycles (10" at 94° C., 30" at 66° C., 2' at 72° C.). For further concentration, one aliquot from this reaction was subjected to a second PCR with specific nested primers from the kit with 2 minutes' elongation time at 72° C., 10 cycles (10" at 94° C., 30" at 66° C., 2' at 72° C.). The product resulting from this reaction was ligated into 3 different, individually modified pCR3.1(+) vectors (InVitrogen): vector (1.ORF), vector (2.ORF) and vector (3.ORF) (FIG. 5: CMV Cytomegalovirus; BGH Bovine Growth Hormone; ORF Open Reading Frame) and then transformed into competent *E. coli* (OneShot™, Invitrogen). These vectors allow expression in eukaryotic cells in 3 different reading frames.

To construct the 3 vectors, the pCR3.1(+)-vector (InVitrogen) was cut with NheI and HindIII (Promega) and ligated with one dsDNA oligomer which was produced by annealing two ssDNA oligomers (SEQ ID NO:4 and 5; vector ORF1) or (SEQ ID NO:6 and 7; vector ORF2) or (SEQ ID NO:8 and 9; vector ORF3), using standard methods (e.g. Ausubel et al., 1994; Sambrook et al. 1989 ColdSpring Harbor Laboratory Press). The 3 vector types have a start codon and a cloning site for expression in a reading frame which is different from the other two vectors.

The transformation of competent *E. coli* (OneShot™, Invitrogen) carried out in three batches (vector 1.ORF, 2.ORF and 3.ORF) with the cDNA of the subtractive cDNA library produced about 9600 clones. These were examined by PCR analysis for the presence and length of the insert cDNA. The following method was used: the 9600 clones were cultivated in 96-well blocks in LB-Amp medium for 48 h at 37° C. Then 5 µl aliquots of the *E. coli* suspensions were heated to 100° C. in 500 µl of TE buffer for 10 minutes and 1.5 µl thereof were used as the basis for a PCR in which the insert of the vector was amplified with flanking primers (SEQ ID NO:10 and 11) over 35 cycles (1' at 94° C., 1' at 55° C., 2' at 72° C.). The PCR products were revealed by agarose-gel electrophoresis and ethidium bromide staining. The bacterial cultures remaining were stored as glycerol stock cultures at −80° C.

A cDNA subtraction library of 3450 individual clones was obtained in the form of *E. coli* glycerol stock cultures, the insert length of which was known from agarose gel electrophoresis. As expected, the inserted cDNA fragments were shown to have an average length of about 800 bp.

EXAMPLE 3
DNA Sequencing and Annotation of Clones of the Subtractive cDNA Library of the Pancreatic Tumour Cell Line MZ.PC2 m7#1 B7.1#3

The plasmid-DNA from 50 clones randomly selected from the subtractive cDNA library were isolated in accordance with the manufacturer's instructions (QIAgen) and sequenced by the Sanger method on an ABI-Prism apparatus. The sequences thus found were annotated by BLAST-Search (National Center for Biotechnology Information) and subjected to EST data bank comparisons. This made it possible to identify 38 known and 12 unknown genes. For the latter there were only EST entries. For the 12 unknown genes the expression profile was estimated: the starting tissue for the corresponding cDNA library was checked for all the ESTS in data banks having greater than 95% identity (BLAST) with the experimentally determined sequence. They were subdivided into i) critical normal tissue, ii) foetal, "non-essential" and immunoprivileged tissue and iii) tumours and tumour cell lines. On the basis of this "virtual mRNA profile" 4 clones (R2, R8, R11 and R12) were selected for further experimental analysis.

Figure 1B:
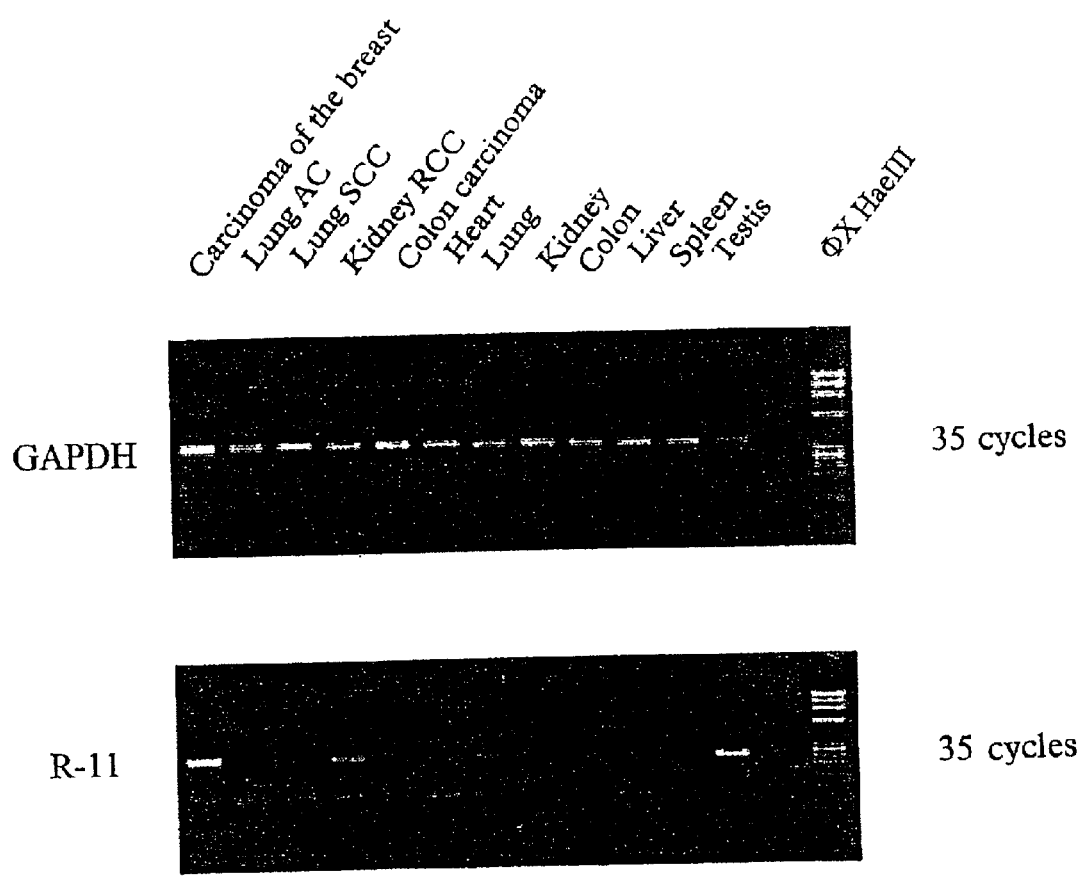
Figure 2:
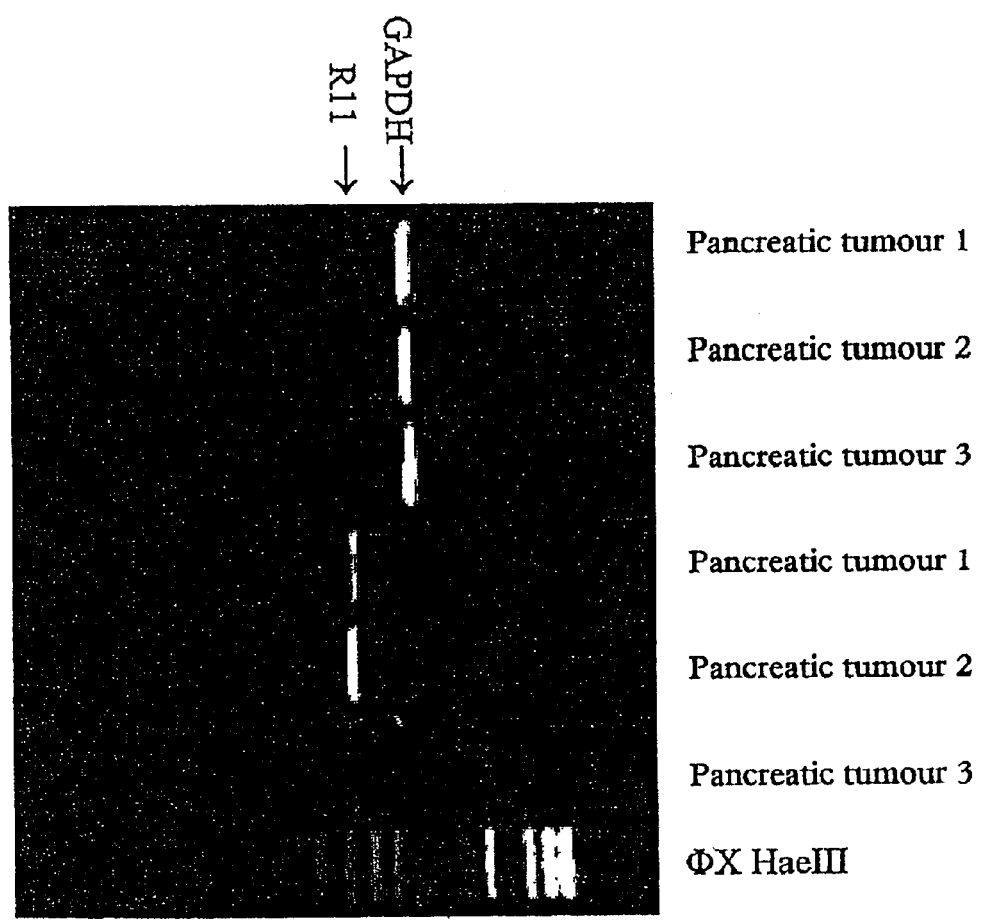
FIG. 2: Transcription of R11 in tumour tissues and normal tissues: Qualitative PCR
Figure 4:
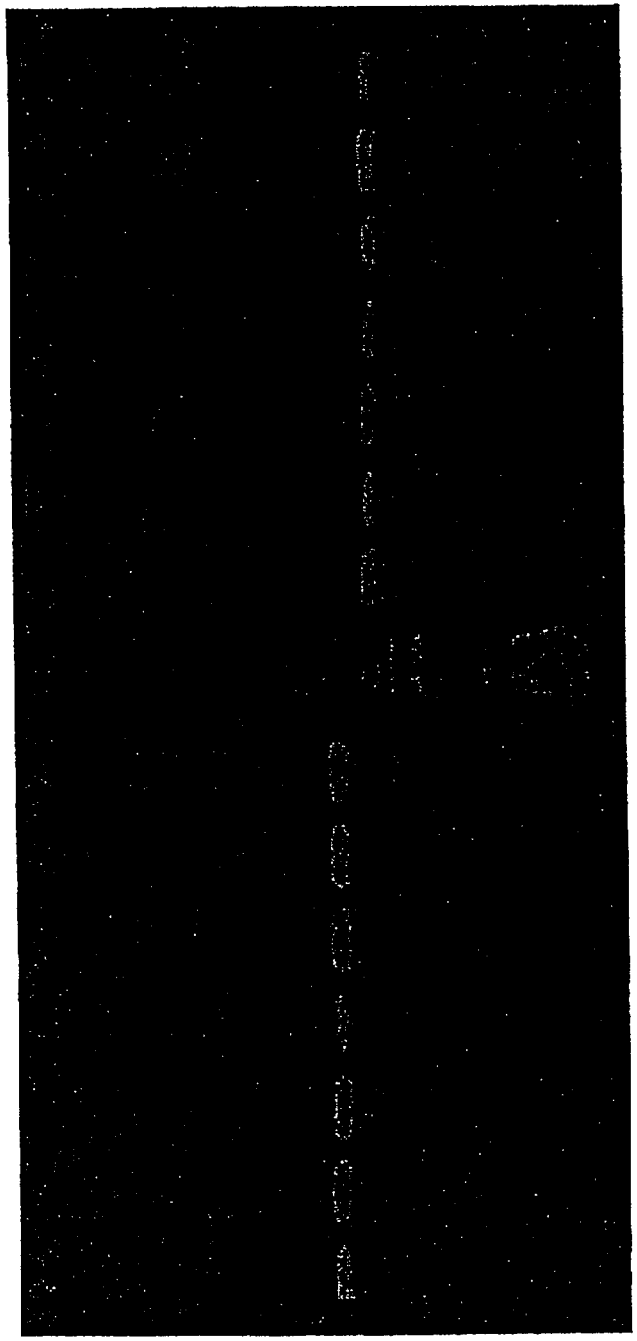
FIG. 4: Transcription of R11 Qualitative RT-PCR from RNA from human tumour cell lines

EXAMPLE 4
Transcriptional Analysis of the Candidate Clones in Tumour and Normal Tissue Between 2 and 5 µg of total RNA from tumour or normal tissues were reverse transcribed using SuperScriptII (GibcoBRL) or AMV-RT (Promega) in accordance with the manufacturer's recommendations. For each individual RNA probe a second test was carried out without reverse transcriptase as a control for contamination by chromosomal DNA. The quality and quantity of the cDNAs was checked by PCR with γ-actin-specific primers (SEQ ID NO: 14 and 15) and GAPDH specific primers (SEQ ID NO:16 and 17) after 30 and 35 cycles (1' at 95° C., 1' at 55° C., 1' at 72° C.). The 4 candidate genus were analysed analogously with specific primers. The PCR products were detected by agarose gel electrophoresis and ethidium bromide staining. A candidate which was designated "R11" exhibited a relatively specific tumour/testis transcription profile, after 35 cycles with R11-specific primers (SEQ ID NO:12 and 13); the semiquantitative RT-PCR of RNA from carcinoma of the breast, adenocarcinoma of the lung, plate epithelial carcinoma of the lung, carcinoma of the kidney, colon carcinoma, heart, lung, liver, kidney, colon, spleen and testis is shown in FIG. 1. Another qualitative PCR of cDNA from the tissue of 3 human patients with tumours of the pancreas using the same R11-specific primers (SEQ ID NO:12 and 13) showed expression in human pancreatic tumours (FIG. 2). Moreover, an additional qualitative PCR of cDNA from various tumour cell lines from human lung (LC 6, 16), gall bladder (GB 1) and pancreatic tumours (PC 1, 2) and two melanomas (Mel 2, 7) was carried out with the same R11-specific primers (SEQ ID NO:12 and 13), which showed clear expression in all the tumour cell lines (FIG. 4). In this analysis the Perkin Elmer method (GeneAmp RNA PCR Kit, #N808-0017) was used (RT reaction: (1×) 15'/42° C.–5'/99° C.–5'/4° C.; PCR reaction: (35×) 2'/95° C.–1'/95° C.–1'/60° C. and (1×) 7'/72° C.–4° C. (FIG. 4). As described above, the PCR products were revealed by agarose gel electrophoresis and ethidium bromide staining. A 1 kb size marker made by Gibco BRL was used as the size marker.

EXAMPLE 5
Transcription Profile of R11 in Normal Tissues

Figure 3:
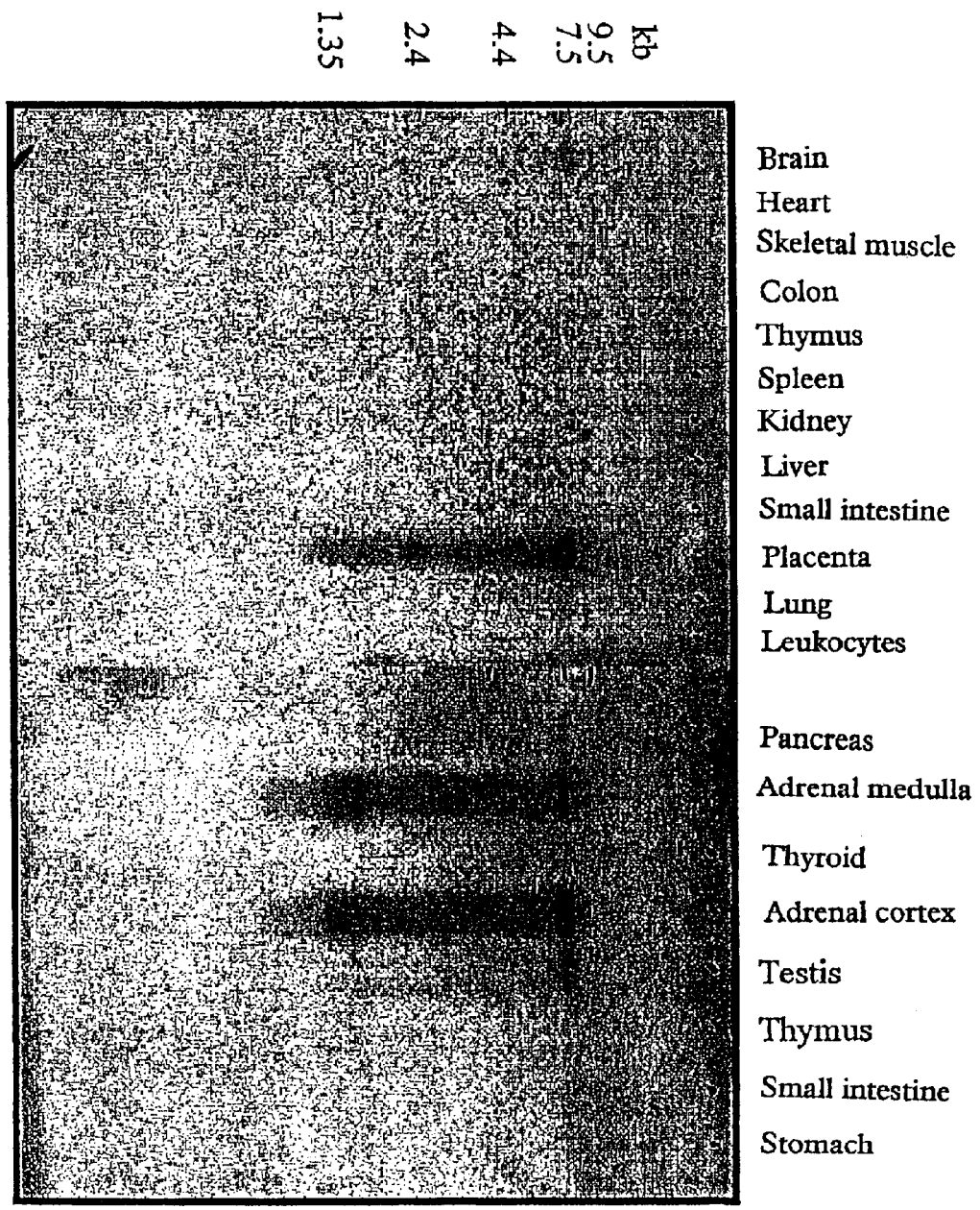
FIG. 3: Northern Blot analysis of R11 in normal tissues

For Northern Blot analysis, Human Multiple Tissue Northern Blots (Clontech, Palo Alto and Invitrogen) were hybridised for 2 h at 68° with the roughly 1000 bp long R11 PCR product labelled with [α-$^{32}$P]dCTP (NEN, Boston). Visualisation was carried out by standard autoradiography (Hyperfilm, Amersham). FIG. 3 shows the results of this analysis: from 19 normal tissues (pancreas, adrenal medulla, thyroid, adrenal cortex, testes, thymus, small intestine, stomach, brain, heart, skeletal muscle, colon, spleen, kidney, liver, placenta, lung, leukocytes). For R11, a prominent transcript 7.5 kb long is found in the placenta, adrenal medulla, adrenal cortex and in the testis. A very weak band of 7.5 kb can also be detected in the brain. Since all these normal tissues have immunoprivileged status (Streilein, 1995, Science 270: 1158–1159) an attack by CTL can be ruled out in any immunotherapy based on this antigen.

Other transcripts of 3.8 kb and 2.3 kb, which might possibly be splice variants of the 7.5 kb transcript or might be derived from a homologous gene, were identified in the adrenal medulla and adrenal cortex (FIG. 3).

EXAMPLE 6
Cloning the R11 cDNA

The following procedure was used to clone the human R11 cDNA: a BLAST search identified a fragment AF038197 and a plurality of ESTs, such as for example N42343, W69539, H82474, H51766, N28313, overlapping with the R11 "original sequence" (796 bp) obtained in Example 3 by sequencing. Starting from the sequence AF038197 a contig overlapping with the clone R11 was found with the EstExtractor on TigemNet (http://gcg.tigem.it/cgi-bin/uniestass.pl, Banfi et al., 1996, Nature Genetics 13:167–174). The overlapping of the contig and the "original sequence" of the 796 bp long R11 was verified by PCR amplification with an R11 "original sequence"—specific primer and a primer located on the contig (SEQ ID NO: 18 and 19) from a SuperScript™ Human Testis cDNA Library (GibcoBRL) and subsequent sequencing. By means of a PCR with an R11-specific primer (SEQ ID NO:20) and a vector-specific primer (SEQ ID NO:21), other fragments belonging to R11 were amplified from the SuperScript™ Human Testis cDNA Library using the Advantage cDNA PCR Kit (Clontech) and following the standard procedure described therein. Knowledge of these new sequences in turn made it possible to carry out further PCRs with R11-specific primers (SEQ ID NO: 22 and 23) and the vector-specific primer (SEQ ID NO:21).

To extend the R11-cDNA further, a human testis Rapid-Screening cDNA Library panel (OriGene Technologies, Inc) was screened with primers specific to R11 (SEQ ID NO: 24 and 25) under the standard PCR conditions specified by the manufacturer. From the positive wells, one aliquot was amplified as a template for a PCR with an R11 specific primer and a primer specific to the vector (SEQ ID NO: 26 and 27) using the Advantage cDNA PCR Kit (Clontech) and following the standard procedure described therein.

For the sequence analysis, aliquots of the PCR preparations were ligated directly into the pCR2.1 vector (Invitrogen) and then transformed into competent E. coli (OneShot™, Invitrogen) and sequenced as described in Example 3.

Starting from these newly identified sequences, 5'-sequence regions located higher upstream could be cloned from a SuperScript™ Human Testis cDNA Library (GibcoBRL) with the following additional oligonucleotide primers specific for R11 (SEQ ID NOs:28 to 43). The primers were used with a plasmid-specific primer (SEQ ID NO:21) described hereinbefore or combined with one another for the PCR cloning using the Advantage cDNA PCR Kit (Clontech).

The cloned region of the R11-cDNA has 6582 bp, whilst the presence of a PolyA tail at the 3'-end of the sequence is an indication of the completeness of the cDNA in this region. Two separate continuous reading frames were identified. The first reading frame at the 5' end (R11-ORF-1; SEQ ID NO:2) is represented by the start codon at position 218 and the stop codon (TAG) at position 1421 in SEQ ID NO:1. There are no data bank entries of known genes for this gene. Analysis of the protein profile (http://www.expasy.ch/prosite, Hofmann et al., 1999, Nucleic Acid Res. 27:215–219) yielded a reference to three possible N-glycosylation sites (position #62–65, 76–79 and 117–120 in SEQ ID NO: 2), a cAMP- and cGMP-dependent protein kinase phosphorylation site (position #11–14 in SEQ ID NO.2), as well as 7 possible PKC-phosphorylation sites (position #9–11, 14–16, 78–80, 119–121, 183–185, 202–204 and 210–212 in SEQ ID NO:2) and 6 possible casein kinase II phosphorylation sites (position #119–122, 127–130, 183–186, 256–259, 295–298 and 358–361 in SEQ ID NO:2). The zinc finger motif (zf-CCHC; E=0,11, Pfam-A HMM) from position #371 to position #384 in SEQ ID NO:2 (<u>C</u>LY<u>C</u>GTGG<u>H</u>YADN<u>C</u>) should be of particular interest for predicting a possible function of R11-ORF-1. It is known that members of the protein family which have these motifs do not have any insertions or deletions in the motif itself; this is also true of the R11-ORF-1 protein. Although no typical SH3 binding sequence can be found, it is certainly conceivable that the P-rich region (position #36–56 in SEQ ID NO:2) could interact with an SH3 domain. By using the COILS algorithm, a coiled-coil structure can be predicted with more than 99% probability for the amino acid groups in the region of position #80 to about 125. On the basis of these two domains, the zinc finger motif and the coiled coil domain, it can be concluded that R11-ORF-1 is possibly a transcription factor the oligomerisation of which is controlled via these two domains.

In the second open reading frame, R11-ORF-2, which is defined by a start codon at position #1498 and a stop codon (TAA) at 2569, in addition to the two obvious proline-rich sections (position #128–141 and 330–351 in SEQ ID NO: 2), potential motifs for two N-glycosylation sites (104–107 and 251–254), one protein kinase C phosphorylation site (108–110), five casein kinase II phosphorylation sites (99–102, 165–168, 198–201, 200–203 and 274–277) and a region resembling the active centre of eukaryotic and viral aspartate proteinases (16–27). The clear homology of the first 280 amino acids of R11-ORF-2 with the retroviral pol polyprotein is particularly remarkable. In the C-terminus, by contrast, no homologies could be discovered. Amino acids from position #9 to 277 clearly align in blastp with the Fugu pol polyprotein (position #104–365; $2e^{-22}$). The aspartate protease pattern #16–27 mentioned above comprises the active nucleophil Asp (#19) of the active centre of the protease of the pol region; position #215 to #277 corresponding to part of the reverse transcriptase domain. The protein derived from R11-ORF-2 is therefore a possible retrotransposon.

EXAMPLE 7

Potential MHC-binding Peptides in the Regions Coding for the Two Reading Frames of R11, R11-ORF-1 and R11-ORF-2

Potential peptide epitopes within the two reading frames of R11 according to SEQ ID NO:2 or 3) were carried out using the algorithms described by Parker et al., 1994, J. Immunol. 152: 163 on the basis of known motifs (Rammensee et al., 1995, Immunogenetics 41: 178–228). 9-mer candidate peptides have been identified for the most important HLA-types, especially for HLA-A1, -A*0201, -A3, -B7, -B14 and -B*4403, which can be expected to bind to the corresponding HLA molecules and thus constitute immunogenic CTL-epitopes; the peptides discovered are listed in Table 1 (R11-ORF-1) and Table 2 (R11-ORF-2). By analogous methods, other potential peptide epitopes may be found for other HLA types or 8-, 9-, or 10-mer peptides.

TABLE 1

Immunogenic peptide candidates of R11-ORF-1 (401 amino acids)

| Starting position in SEQ ID NO:2 | Sequence | HLA |
|---|---|---|
| 35 | Ser Pro Pro Thr Pro Thr Val Thr Leu (SEQ ID NO:88) | HLA-B7 |
| 85 | Leu Ser Glu Glu Ile Asn Asn Leu Arg (SEQ ID NO:89) | HLA-A1 |
| 112 | Lys Leu Thr Glu Glu Asn Thr Thr Leu (SEQ ID NO:90) | HLA-A*0201 |
| 113 | Leu Thr Glu Glu Asn Thr Thr Leu Arg (SEQ ID NO:91) | HLA-A1 |
| 135 | Ile Glu Leu Arg Gly Ala Ala Ala Ala (SEQ ID NO:92) | HLA-B*4403 |
| 172 | Phe Met Ala Gln Cys Gln Ile Phe Met (SEQ ID NO:93) | HLA-A*0201 |
| 199 | Ser Met Met Thr Gly Arg Ala Ala Arg (SEQ ID NO:94) | HLA-A3 |
| 205 | Ala Ala Arg Trp Ala Ser Ala Lys Leu (SEQ ID NO:95) | HLA-B7 |

TABLE 1-continued

Immunogenic peptide candidates of R11-ORF-1 (401 amino acids)

| Starting position in SEQ ID NO:2 | Sequence | HLA |
|---|---|---|
| 211 | Ala Lys Leu Glu Arg Ser His Tyr Leu (SEQ ID NO:96) | HLA-B14 |
| 252 | Gln Gly Met Gly Ser Val Ile Asp Tyr (SEQ ID NO:97) | HLA-B*4403 |
| 274 | Asn Glu Pro Ala Leu Ile Asp Gln Tyr (SEQ ID NO:98) | HLA-B*4403 |
| 315 | Arg Arg Leu Ala Arg Ala Ala Ala Ala (SEQ ID NO:99) | HLA-B14 |
| 325 | Lys Pro Arg Ser Pro Pro Arg Ala Leu (SEQ ID NO:100) | HLA-B7 |
| 354 | Arg Met Arg Leu Thr Gln Glu Glu Lys (SEQ ID NO:101) | HLA-A3 |
| 346 | Pro Thr Glu Pro Val Gly Gly Ala Arg (SEQ ID NO:102) | HLA-A1 |

TABLE 2

Immunogenic peptide candidates of R11-ORF-2 (357 amino acids)

| Starting position in SEQ ID NO:3 | Sequence | HLA |
|---|---|---|
| 1 | Met Leu Gln Ile His Leu Pro Gly Arg (SEQ ID NO:44) | HLA-A3 |
| 4 | Ile His Leu Pro Gly Arg His Thr Leu (SEQ ID NO:45) | HLA-A*0201, HLA-B14 |
| 5 | His Leu Pro Gly Arg His Thr Leu Phe (SEQ ID NO:46) | HLA-A3 |
| 31 | Tyr Val Ala Gln Asn Gly Ile Pro Leu (SEQ ID NO:47) | HLA-B7 |
| 39 | Leu Arg Ile Lys Asp Trp Pro Ile Leu (SEQ ID NO:48) | HLA-B14 |
| 46 | Ile Leu Val Glu Ala Ile Asp Gly Arg (SEQ ID NO:49) | HLA-A3 |
| 53 | Gly Arg Pro Ile Ala Ser Gly Pro Val (SEQ ID NO:50) | HLA-B14 |
| 64 | Glu Thr His Asp Leu Ile Val Asp Leu (SEQ ID NO:51) | HLA-B14 |
| 71 | Asp Leu Gly Asp His Arg Glu Val Leu (SEQ ID NO:52) | HLA-A*0201, HLA-B7, HLA-B14 |
| 73 | Gly Asp His Arg Glu Val Leu Ser Phe (SEQ ID NO:53) | HLA-B*4403 |
| 85 | Gln Ser Pro Phe Phe Pro Val Val Leu (SEQ ID NO:54) | HLA-B7 |
| 92 | Val Leu Gly Pro Arg Trp Leu Ser Ala (SEQ ID NO:55) | HLA-A 0201 |
| 97 | Trp Leu Ser Ala His Asp Pro Asn Ile (SEQ ID NO:56) | HLA-A*0201 |
| 110 | Arg Ser Ile Val Phe Asp Ser Glu Tyr (SEQ ID NO:57) | HLA-B*4403 |
| 112 | Ile Val Phe Asp Ser Glu Tyr Cys Arg (SEQ ID NO:58) | HLA-A3 |
| 134 | Pro Pro Pro Ala Pro Gln Pro Pro Leu (SEQ ID NO:59) | HLA-B7 |
| 141 | Pro Leu Tyr Tyr Pro Val Asp Gly Tyr (SEQ ID NO:60) | HLA-A3 |
| 150 | Arg Val Tyr Gln Pro Val Arg Tyr Tyr (SEQ ID NO:61) | HLA-A3 |
| 152 | Tyr Gln Pro Val Arg Tyr Tyr Tyr Val (SEQ ID NO:62) | HLA-A*0201 |
| 155 | Val Arg Tyr Tyr Tyr Val Gln Asn Val (SEQ ID NO:63) | HLA-B14 |
| 159 | Tyr Val Gln Asn Val Tyr Thr Pro Val (SEQ ID NO:64) | HLA-A*0201 |
| 169 | Gly His Val Tyr Pro Asp His Arg Leu (SEQ ID NO:65) | HLA-B14 |

TABLE 2-continued

Immunogenic peptide candidates of R11-ORF-2 (357 amino acids)

| Starting position in SEQ ID NO:3 | Sequence | HLA |
|---|---|---|
| 177 | Leu Val Asp Pro His Ile Glu Met Ile (SEQ ID NO:66) | HLA-A*0201, HLA-A1 |
| 183 | Glu Met Ile Pro Gly Ala His Ser Ile (SEQ ID NO:67) | HLA-A*0201 |
| 189 | His Ser Ile Pro Ser Gly His Val Tyr (SEQ ID NO:68) | HLA-A1, HLA-B*4403 |
| 191 | Ile Pro Ser Gly His Val Tyr Ser Leu (SEQ ID NO:69) | HLA-B7, HLA-A*0201 |
| 198 | Ser Leu Ser Glu Pro Glu Met Ala Ala (SEQ ID NO:70) | HLA-A*0201 |
| 199 | Leu Ser Glu Pro Glu Met Ala Ala Leu (SEQ ID NO:71) | HLA-A1 |
| 202 | Pro Glu Met Ala Ala Leu Arg Asp Phe (SEQ ID NO:72) | HLA-B*4403 |
| 203 | Glu Met Ala Ala Leu Arg Asp Phe Val (SEQ ID NO:73) | HLA-A*0201 |
| 206 | Ala Leu Arg Asp Phe Val Ala Arg Asn (SEQ ID NO:74) | HLA-A*0201 |
| 211 | Val Ala Arg Asn Lys Asp Gly Leu (SEQ ID NO:75) | HLA-B7 |
| 223 | Thr Ile Ala Pro Asn Gly Ala Gln Val (SEQ ID NO:76) | HLA-A*0201 |
| 224 | Ile Ala Pro Asn Gly Ala Gln Val Leu (SEQ ID NO:77) | HLA-B7 |
| 231 | Val Leu Gln Val Lys Arg Gly Trp Lys (SEQ ID NO:78) | HLA-A3 |
| 232 | Leu Gln Val Lys Arg Gly Trp Lys Leu (SEQ ID NO:79) | HLA-A*0201, HLA-B14 |
| 258 | Tyr Pro Arg Leu Ser Ile Pro Asn Leu (SEQ ID NO:80) | HLA*7 |
| 266 | Glu Asp Gln Ala His Leu Ala Thr Tyr (SEQ ID NO:81) | HLA-B*4403 |
| 270 | His Leu Ala Thr Tyr Thr Glu Phe Val (SEQ ID NO:82) | HLA-A*0201 |
| 306 | Gly Arg Asp Gly Gln Gly Arg Ser Leu (SEQ ID NO:83) | HLA-B14 |
| 307 | Arg Asp Gly Gln Gly Arg Ser Leu Tyr (SEQ ID NO:84) | HLA-B*4403 |
| 308 | Asp Gly Gln Gly Arg Ser Leu Tyr Val (SEQ ID NO:85) | HLA-B14 |
| 313 | Ser Leu Tyr Val Pro Val Met Ile Thr (SEQ ID NO:86) | HLA-A*0201, HLA-A3 |
| 320 | Ile Thr Trp Asn Pro His Trp Tyr Arg (SEQ ID NO:87) | HLA-A3 |

The present invention is not to be limited in scope by the exemplified embodiments which are intended as illustrations of single aspects of the invention. Indeed various modifications of the invention in addition to those shown and described herein will become apparent to those skilled in the art from the foregoing description and accompanying drawings. Such modifications are intended to fall within the scope of the appended claims.

All publications and patent applications cited herein are incorporated by reference in their entireties.

What is claimed is:

1. A tumor-associated antigen (TAA) comprising the amino acid sequence of SEQ ID NO:2.

2. A tumor-associated antigen (TAA) designated R11-ORF-1 consisting of the amino acid sequence of SEQ ID NO:2.

3. The TAA of claim 1 wherein the TAA induces or augments a humoral immune response.

* * * * *